(12) United States Patent
Bhatnagar et al.

(10) Patent No.: US 7,632,313 B2
(45) Date of Patent: Dec. 15, 2009

(54) DISC REPAIR SYSTEM

(75) Inventors: Mohit K. Bhatnagar, North Potomac, MD (US); Jack Y. Yeh, North Potomac, MD (US); James A. Sack, Elverson, PA (US); Richard W. Woods, Catonsville, MD (US)

(73) Assignee: JMEA Corporation, Rockville, MD (US)

( * ) Notice: Subject to any disclaimer, the term of this patent is extended or adjusted under 35 U.S.C. 154(b) by 297 days.

(21) Appl. No.: 11/117,704

(22) Filed: Apr. 29, 2005

(65) Prior Publication Data

US 2006/0247643 A1   Nov. 2, 2006

(51) Int. Cl.
*A61F 2/44* (2006.01)
(52) U.S. Cl. .................... 623/17.16; 623/17.11
(58) Field of Classification Search ............... 623/17.16; 227/19, 175.1, 177.1, 180.1, 181.1, 901; 606/99, 104, 108, 139, 142, 143, 149, 213, 606/215, 216, 219, 220
See application file for complete search history.

(56) References Cited

U.S. PATENT DOCUMENTS

| | | | |
|---|---|---|---|
| 3,875,595 A | 4/1975 | Froning | |
| 4,006,747 A | 2/1977 | Kronenthal et al. | |
| 4,235,238 A | 11/1980 | Ogiu et al. | |
| 4,448,194 A | 5/1984 | DiGiovanni et al. | |
| 4,471,181 A | 9/1984 | Dennison | |
| 4,533,076 A | 8/1985 | Bourque | |
| 4,573,448 A | 3/1986 | Kambin | |
| 4,621,639 A | 11/1986 | Transue et al. | |
| 4,669,473 A | 6/1987 | Richards et al. | |
| 4,705,040 A | 11/1987 | Mueller et al. | |
| 4,724,840 A | 2/1988 | McVay et al. | |
| 4,873,976 A | 10/1989 | Schreiber | |
| 4,877,172 A | 10/1989 | Franklin et al. | |
| 4,884,572 A | 12/1989 | Bays et al. | |
| 4,997,436 A | 3/1991 | Oberlander | |
| 5,002,562 A | 3/1991 | Oberlander | |

(Continued)

FOREIGN PATENT DOCUMENTS

WO    WO02/058599    8/2002

OTHER PUBLICATIONS

International Search Report from related PCT application (International Application No. PCT/US2006/015960), dated Apr. 23, 2008.

(Continued)

*Primary Examiner*—Eduardo C Robert
*Assistant Examiner*—Tara R George
(74) *Attorney, Agent, or Firm*—Plumsea Law Group, LLC

(57) ABSTRACT

A repair system including a closure prosthesis and deployment device, and associated methods for repairing any imperfection including a flaw, hole, tear, bulge, or, in some cases, a deliberate cut or incision in any tissue including an intervertebral disc. The prosthesis has first and second side portions with a connecting central portion, and is designed to span an imperfection with opposite ends positioned on opposite sides of the imperfection. The prosthesis may include anchoring features including barbs and/or members that extend transversely. The deployment device can include a canula for positioning the prosthesis near the imperfection, and, in some cases, a mechanism that may cause the two sides of the prosthesis to be deployed in a specific order.

19 Claims, 34 Drawing Sheets

U.S. PATENT DOCUMENTS

| | | | |
|---|---|---|---|
| 5,085,661 A | 2/1992 | Moss | |
| 5,154,189 A | 10/1992 | Oberlander | |
| 5,192,326 A | 3/1993 | Bao et al. | |
| 5,290,296 A | 3/1994 | Phillips | |
| 5,290,297 A | 3/1994 | Phillips | |
| 5,395,317 A | 3/1995 | Kambin | |
| 5,425,489 A * | 6/1995 | Shichman et al. | 227/108 |
| 5,439,464 A | 8/1995 | Shapiro | |
| 5,465,895 A * | 11/1995 | Knodel et al. | 227/176.1 |
| 5,470,337 A | 11/1995 | Moss | |
| 5,500,000 A | 3/1996 | Feagin et al. | |
| 5,549,679 A | 8/1996 | Kuslich | |
| 5,601,571 A | 2/1997 | Moss | |
| 5,632,433 A * | 5/1997 | Grant et al. | 227/179.1 |
| 5,643,319 A | 7/1997 | Green et al. | |
| 5,653,928 A | 8/1997 | Schnipke | |
| 5,716,416 A | 2/1998 | Lin | |
| 5,827,298 A | 10/1998 | Hart et al. | |
| 5,836,147 A | 11/1998 | Schnipke | |
| 5,843,084 A | 12/1998 | Hart et al. | |
| 5,931,855 A | 8/1999 | Buncke | |
| 5,941,439 A | 8/1999 | Kammerer et al. | |
| 5,954,747 A | 9/1999 | Clark | |
| 5,976,186 A | 11/1999 | Bao et al. | |
| 5,980,504 A | 11/1999 | Sharkey et al. | |
| 5,993,475 A | 11/1999 | Lin et al. | |
| 5,997,552 A | 12/1999 | Person et al. | |
| 6,010,513 A | 1/2000 | Tormala et al. | |
| 6,039,753 A | 3/2000 | Meislin | |
| 6,074,395 A | 6/2000 | Trott et al. | |
| 6,099,514 A | 8/2000 | Sharkey et al. | |
| 6,110,210 A | 8/2000 | Norton et al. | |
| 6,126,670 A | 10/2000 | Walker et al. | |
| 6,126,682 A | 10/2000 | Sharkey et al. | |
| 6,146,387 A | 11/2000 | Trott et al. | |
| 6,183,518 B1 | 2/2001 | Ross et al. | |
| 6,190,401 B1 | 2/2001 | Green et al. | |
| 6,206,921 B1 | 3/2001 | Guagliano et al. | |
| 6,206,923 B1 | 3/2001 | Boyd et al. | |
| 6,241,747 B1 | 6/2001 | Ruff | |
| 6,245,107 B1 | 6/2001 | Ferree | |
| 6,264,659 B1 | 7/2001 | Ross et al. | |
| 6,270,517 B1 | 8/2001 | Brotz | |
| 6,280,475 B1 | 8/2001 | Bao et al. | |
| 6,290,715 B1 | 9/2001 | Sharkey et al. | |
| 6,306,156 B1 | 10/2001 | Clark | |
| 6,318,553 B1 | 11/2001 | Deschenes | |
| 6,322,563 B1 | 11/2001 | Cummings et al. | |
| 6,332,894 B1 | 12/2001 | Stalcup et al. | |
| 6,387,113 B1 | 5/2002 | Hawkins et al. | |
| 6,387,130 B1 | 5/2002 | Stone et al. | |
| 6,395,031 B1 | 5/2002 | Foley et al. | |
| 6,402,750 B1 | 6/2002 | Atkinson et al. | |
| 6,425,919 B1 | 7/2002 | Lambrecht | |
| 6,427,895 B1 | 8/2002 | Deschenes | |
| 6,428,576 B1 | 8/2002 | Haldimann | |
| 6,443,988 B2 | 9/2002 | Felt et al. | |
| 6,446,854 B1 * | 9/2002 | Remiszewski et al. | 227/175.1 |
| 6,482,235 B1 | 11/2002 | Lambrecht et al. | |
| 6,491,724 B1 | 12/2002 | Ferree | |
| 6,497,707 B1 | 12/2002 | Bowman et al. | |
| 6,508,839 B1 | 1/2003 | Lambrecht et al. | |
| 6,517,568 B1 | 2/2003 | Sharkey et al. | |
| 6,530,933 B1 | 3/2003 | Yeung et al. | |
| 6,551,343 B1 | 4/2003 | Tormala et al. | |
| 6,562,033 B2 | 5/2003 | Shah et al. | |
| 6,564,939 B1 | 5/2003 | Deschenes et al. | |
| 6,569,369 B2 | 5/2003 | Shilale et al. | |
| 6,579,291 B1 | 6/2003 | Keith et al. | |
| 6,592,625 B2 | 7/2003 | Cauthen | |
| 6,596,008 B1 | 7/2003 | Kambin | |
| 6,596,014 B2 | 7/2003 | Levinson et al. | |
| 6,599,310 B2 | 7/2003 | Leung et al. | |
| 6,602,291 B1 | 8/2003 | Ray et al. | |
| 6,638,276 B2 | 10/2003 | Sharkey et al. | |
| 6,666,872 B2 | 12/2003 | Barreiro et al. | |
| 6,676,678 B2 * | 1/2004 | Gifford et al. | 606/184 |
| 6,682,535 B2 | 1/2004 | Hoogland | |
| 6,685,077 B1 | 2/2004 | Davignon et al. | |
| 6,689,125 B1 | 2/2004 | Keith et al. | |
| 6,692,499 B2 | 2/2004 | Tormala et al. | |
| 6,726,685 B2 | 4/2004 | To et al. | |
| 6,733,496 B2 | 5/2004 | Ashley et al. | |
| 6,733,531 B1 | 5/2004 | Trieu | |
| 6,736,815 B2 | 5/2004 | Ginn | |
| 6,746,685 B2 | 6/2004 | Williams | |
| 6,779,701 B2 | 8/2004 | Bailly et al. | |
| 6,848,152 B2 | 2/2005 | Genova et al. | |
| 7,004,970 B2 | 2/2006 | Cauthen, III et al. | |
| 7,056,330 B2 * | 6/2006 | Gayton | 606/219 |
| 2001/0004710 A1 | 6/2001 | Felt et al. | |
| 2001/0010021 A1 | 7/2001 | Boyd et al. | |
| 2002/0019626 A1 | 2/2002 | Sharkey et al. | |
| 2002/0019636 A1 * | 2/2002 | Ogilvie et al. | 606/75 |
| 2002/0022830 A1 | 2/2002 | Sharkey et al. | |
| 2002/0026195 A1 | 2/2002 | Layne et al. | |
| 2002/0068974 A1 | 6/2002 | Kuslich et al. | |
| 2002/0111688 A1 | 8/2002 | Cauthen | |
| 2002/0120337 A1 | 8/2002 | Cauthen | |
| 2002/0123807 A1 | 9/2002 | Cauthen, III | |
| 2002/0147461 A1 | 10/2002 | Aldrich et al. | |
| 2002/0147479 A1 | 10/2002 | Aldrich | |
| 2002/0147496 A1 | 10/2002 | Belef et al. | |
| 2002/0147497 A1 | 10/2002 | Belef et al. | |
| 2002/0151976 A1 | 10/2002 | Foley et al. | |
| 2002/0151979 A1 | 10/2002 | Lambrecht et al. | |
| 2002/0151980 A1 | 10/2002 | Cauthen | |
| 2002/0156530 A1 | 10/2002 | Lambrecht et al. | |
| 2002/0156531 A1 | 10/2002 | Felt et al. | |
| 2002/0165542 A1 | 11/2002 | Ferree | |
| 2002/0173851 A1 | 11/2002 | McKay | |
| 2002/0183848 A1 | 12/2002 | Ray et al. | |
| 2002/0189622 A1 | 12/2002 | Cauthen, III et al. | |
| 2002/0198599 A1 | 12/2002 | Haldimann | |
| 2003/0009227 A1 | 1/2003 | Lambrecht et al. | |
| 2003/0014117 A1 | 1/2003 | Lambrecht et al. | |
| 2003/0014118 A1 | 1/2003 | Lambrecht et al. | |
| 2003/0028251 A1 | 2/2003 | Mathews | |
| 2003/0040796 A1 | 2/2003 | Ferree | |
| 2003/0069641 A1 | 4/2003 | Reuter et al. | |
| 2003/0074075 A1 | 4/2003 | Thomas, Jr. et al. | |
| 2003/0078579 A1 | 4/2003 | Ferree | |
| 2003/0082169 A1 | 5/2003 | Boyd | |
| 2003/0083642 A1 | 5/2003 | Boyd et al. | |
| 2003/0093155 A1 | 5/2003 | Lambrecht et al. | |
| 2003/0114930 A1 | 6/2003 | Lim et al. | |
| 2003/0120345 A1 | 6/2003 | Cauthen | |
| 2003/0125748 A1 | 7/2003 | Li et al. | |
| 2003/0125807 A1 | 7/2003 | Lambrecht et al. | |
| 2003/0153976 A1 | 8/2003 | Cauthen, III et al. | |
| 2003/0158604 A1 | 8/2003 | Cauthen, III et al. | |
| 2003/0163200 A1 | 8/2003 | Cauthen | |
| 2003/0181964 A1 | 9/2003 | Sharkey et al. | |
| 2003/0181983 A1 | 9/2003 | Cauthen | |
| 2003/0187445 A1 | 10/2003 | Keith et al. | |
| 2003/0187507 A1 | 10/2003 | Cauthen | |
| 2003/0187508 A1 | 10/2003 | Cauthen | |
| 2003/0191536 A1 | 10/2003 | Ferree | |
| 2003/0195514 A1 | 10/2003 | Trieu et al. | |
| 2003/0195628 A1 | 10/2003 | Bao et al. | |
| 2003/0195630 A1 | 10/2003 | Ferree | |
| 2003/0199979 A1 | 10/2003 | McGuckin, Jr. | |
| 2003/0199984 A1 | 10/2003 | Trieu | |
| 2003/0220649 A1 | 11/2003 | Bao et al. | |

| | | |
|---|---|---|
| 2003/0220690 A1 | 11/2003 | Cauthen, III |
| 2003/0220693 A1 | 11/2003 | Cauthen, III |
| 2003/0220694 A1 | 11/2003 | Cauthen, III |
| 2003/0220695 A1 | 11/2003 | Sevrain |
| 2004/0002746 A1 | 1/2004 | Ryan et al. |
| 2004/0002760 A1 | 1/2004 | Boyd et al. |
| 2004/0002763 A1 | 1/2004 | Phillips et al. |
| 2004/0002764 A1 * | 1/2004 | Gainor et al. ............ 623/17.16 |
| 2004/0010317 A1 | 1/2004 | Lambrecht et al. |
| 2004/0019381 A1 | 1/2004 | Pflueger |
| 2004/0024463 A1 | 2/2004 | Thomas, Jr. et al. |
| 2004/0024465 A1 | 2/2004 | Lambrecht et al. |
| 2004/0030392 A1 | 2/2004 | Lambrecht et al. |
| 2004/0034429 A1 | 2/2004 | Lambrecht et al. |
| 2004/0039392 A1 | 2/2004 | Trieu |
| 2004/0044412 A1 | 3/2004 | Lambrecht et al. |
| 2004/0059417 A1 | 3/2004 | Smith et al. |
| 2004/0059418 A1 | 3/2004 | McKay et al. |
| 2004/0064023 A1 | 4/2004 | Ryan et al. |
| 2004/0068268 A1 | 4/2004 | Boyd et al. |
| 2004/0073308 A1 | 4/2004 | Kuslich et al. |
| 2004/0083002 A1 | 4/2004 | Belef et al. |
| 2004/0092933 A1 | 5/2004 | Shaolian et al. |
| 2004/0092945 A1 | 5/2004 | Ferree |
| 2004/0097924 A1 | 5/2004 | Lambrecht et al. |
| 2004/0097980 A1 | 5/2004 | Ferree |
| 2004/0102774 A1 | 5/2004 | Trieu |
| 2004/0267309 A1 * | 12/2004 | Garvin ....................... 606/217 |

OTHER PUBLICATIONS

Office Action from U.S. Appl. No. 11/379,940 mailed Sep. 21, 2007.
Response to Office Action filed on Jan. 22, 2008 for U.S. Appl. No. 11/379,940.
Final Office Action from U.S. Appl. No. 11/379,940 mailed Apr. 30, 2008.
Amendment Filed with Request for Continuing Exam on Jun. 24, 2008 for U.S. Appl. No. 11/379,940.
Notice of Allowability from U.S. Appl. No. 11/324,765 mailed Feb. 24, 2009.
Amendment Pursuant to 37 C.F.R. 1.312 filed on Mar. 3, 2009 for U.S. Appl. No. 11/324,765.
Notice of Allowance from U.S. Appl. No. 11/324,765 mailed Mar. 9, 2009.

* cited by examiner

DISC REPAIR SYSTEM

BACKGROUND OF THE INVENTION

1. Field of the Invention

The invention relates generally to medical devices, and more particularly, to medical devices for repair of tissue, including intervertebral discs.

2. Description of Related Art

The spinal cord is the body's main nerve pathway, extending from the base of the skull down the back toward the lower (sacral) region of the back, where it branches. The spinal cord is protected from injury and damage by the vertebral column, a flexible column comprised of bones called vertebrae, which encircle and enclose the spinal column. Most of the vertebrae in the spinal column are interspersed with intervertebral discs, which are compliant discs, each approximately 1.0 cm to 1.5 cm thick. The discs are disposed between adjacent vertebrae in the spinal column and allow limited motion and rotation between those adjacent vertebrae. The cumulative effect of the motion provided by the disc allows the spinal column to flex and move. The discs also act as shock absorbers. The intervertebral discs themselves are comprised of a relatively tough outer layer called the nucleus purposus 222, inside of which is a soft, gel-like center called the nucleus purposus 224.

FIG. 1 is a plan view of a single vertebra, shown generally at 200, and its associated intervertebral disc 202. (The anatomy shown in FIG. 1 is generally that of a lumbar vertebra, although the anatomy of thoracic and lumbar vertebra is similar; therefore, FIG. 1 can be considered to illustrate the basic principles of both thoracic and lumbar vertebral anatomy.) The spinous process 206 of the vertebra 200 extends dorsally and can typically be palpated and felt through the skin of the back. Also in the dorsally-extending portion of the vertebra 200 are two transverse processes 208 and two mammillary processes and facet joints 212. A spinal canal 214 (i.e., an opening) is provided in the vertebra 200. The spinal cord and nerves 216 extend through the spinal canal 214 such that the spinal cord 216 receives the full protection of the bony, dorsally-located spinous, transverse, and mammillary processes and facet joints 206, 208, 212. The vertebral body also protects the spinal cord and nerves 216 ventrally. Periodically, nerves 218 branch out from the spinal cord 216 to innervate various areas of the body. The forward or ventral edge of the vertebral foramen 221 (see FIGS. 1 and 2) is defined by the vertebral body (not shown in FIG. 1), a bony, generally elliptical shelf in front of which the intervertebral disc 202 rests. FIG. 1 also illustrates the basic structure of the intervertebral disc 202, including the nucleus purposus 222 and the nucleus pulposus 224.

The vertebrae and the intervertebral discs are usually in good alignment, e.g., as shown in FIG. 1, and the intervertebral discs normally perform their function without incident. However, there are certain conditions, notably traumatic injury and vertebral column degeneration, that can cause problems. For example, if a weak spot develops in the nucleus purposus, the pressure on the disc may cause the nucleus purposus 224 to be pushed through the weak spot, a condition called herniation. This reduces the shock-absorbing ability of the disc, and may impinge on spinal or surrounding nerves, causing pain and possibly sensory or motor problems. Moreover, trauma may cause an intervertebral disc to fail entirely, potentially causing all of the above problems, even if a particular weak spot in the nucleus purposus has not developed.

FIG. 2 is a plan view similar to that of FIG. 1, illustrating a herniated or traumatized intervertebral disc 202. As shown, the nucleus pulposus 224 is protruding from the intervertebral disc 202 through a cut or flaw 204 in the intervertebral disc 202. The protruding nucleus pulposus 224 impinges on one of the exiting nerves 218 as well as the spinal cord 216 or cauda equina.

If an intervertebral disc has failed or become herniated, a typical correction is a surgical procedure to remove some or all of the herniated portion (or the protruding nucleus purposus 224) but no attempt is made to repair the nucleus purposus by surgically closing any hole or incision. FIG. 3 is a plan view similar to that of FIG. 1 showing partial results of a typical repair procedure in which the protruding nucleus pulposus 224 is removed and, depending on the procedure, the cut, incision, tear, or flaw 204 may be altered or neatened so as to provide for easier closure. In the view of FIG. 3, the cut, incision, tear, or flaw 204 is still open.

Any surgery to the vertebral column can be traumatic for the patient, and, depending on the area of the intervertebral column that is to be repaired, it can be difficult to access the area to make repairs. It is very difficult to close the nucleus purposus effectively; therefore no attempt is currently made to close or repair this defect.

SUMMARY OF THE INVENTION

One aspect of the invention relates to a method for repairing an imperfection in a disc associated with a spinal column. The term, "imperfection" refers to any irregularity including a flaw, hole, tear, bulge, or, in some cases, a deliberate cut or incision. The method comprises inserting a first end portion of a prosthesis into a first portion of the disc. The prosthesis has a central portion connected to the first end portion and a second end portion connected to the central portion. The first end portion of the prosthesis has a first anchoring device and the second end portion of the prosthesis has a second anchoring device. The first end portion of the prosthesis is associated with first portion of the disc that is on a first side of the cut. The method also comprises associating the second end portion of the prosthesis into a second portion of the disc that is circumferentially spaced from the first portion of the disc. The second portion of the disc is on a second side of the cut. The central portion of the prosthesis spans the cut and inserting the second end of the prosthesis farther into the disc draws the first side of the cut closer to the second side of the cut.

In some embodiments, the first anchor may include at least one projection extending away from the first end portion. The second anchor may include at least one barb. The prosthesis, in an installed position, may provide a circumferential force on the disc. The prosthesis may provide a hoop stress on the disc. The prosthesis may help to maintain or help to increase the axial height of the disc. The prosthesis may help to close the cut on the disc, and may also help to maintain nucleus material within the disc. It is also possible to provide an optional additional prosthesis in roughly the same location as the previous prosthesis. This additional prosthesis can be disposed at an angle different than the angle of the previous prosthesis. In some cases, the additional prosthesis can be vertically disposed.

In another aspect, the invention can be used on any imperfection of any tissue.

In another aspect, the invention is used to join two different types of tissue.

Another aspect of the invention relates to a system configured to deliver a prosthesis to a disc of a mammal. The system comprises a first penetrating member carrying a first portion of the prosthesis, and a second penetrating member spaced from the first penetrating member and carrying a second portion of the prosthesis. A first rod is associated with the first penetrating member and is configured to move the first portion of the prosthesis with respect to the first penetrating member. A second rod is associated with the second penetrating member and is configured to move the second portion of the prosthesis with respect to the second penetrating member. Motion of the first rod is capable of ejecting the first portion of the prosthesis from the first penetrating member, and motion of the second rod is capable of ejecting the second portion of the prosthesis from the second penetrating member.

In another aspect, the second rod may have a range of motion greater than or equal to that of the first rod.

In another aspect, the first penetrating member may be disposed coaxially outward of the first rod and the second penetrating member may be disposed coaxially outward of the second rod.

In another aspect, the first penetrating member and the second penetrating member may both be associated with a pushing member.

In another aspect, the pushing member may be associated with a first trigger, such that motion of the first trigger moves the pushing member. The first rod may be connected to a first follower, the first follower interacting with a first cam.

In another aspect, the second rod may be connected to a second follower, the second follower interacting with a second cam.

In another aspect, the first cam and the second cam may be associated with a second trigger, such that motion of the second trigger moves the first cam and the second cam.

In another aspect, the first cam may be shaped differently from the second cam, and the different shapes of the first cam and the second cam may cause the first follower to move differently than the second follower.

In another aspect, the first follower may move a first predetermined distance and then cease to move after achieving the first predetermined distance. In some cases, the first predetermined distance may approximate half of a length of a first anchor associated with the first end portion. In some cases, the second follower may move farther than the first follower.

In another aspect, the first penetrating member may include a first groove, and the first end portion of the prosthesis may be disposed in the first groove. The second penetrating member may include a second groove and the second end portion of the prosthesis may be disposed in the second groove.

In another aspect, the first rod may be disposed in the first groove and may engage the first end portion of the prosthesis disposed in the first groove. The second rod may be disposed in the second groove and may engage the second end portion of the prosthesis disposed in the second groove.

Other systems, methods, features and advantages of the invention will be, or will become, apparent to one with skill in the art upon examination of the following figures and detailed description. It is intended that all such additional systems, methods, features and advantages be included within this description, be within the scope of the invention, and be protected by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like reference numerals designate corresponding parts throughout the different views.

DETAILED DESCRIPTION OF THE PREFERRED EMBODIMENTS

Figure 1:
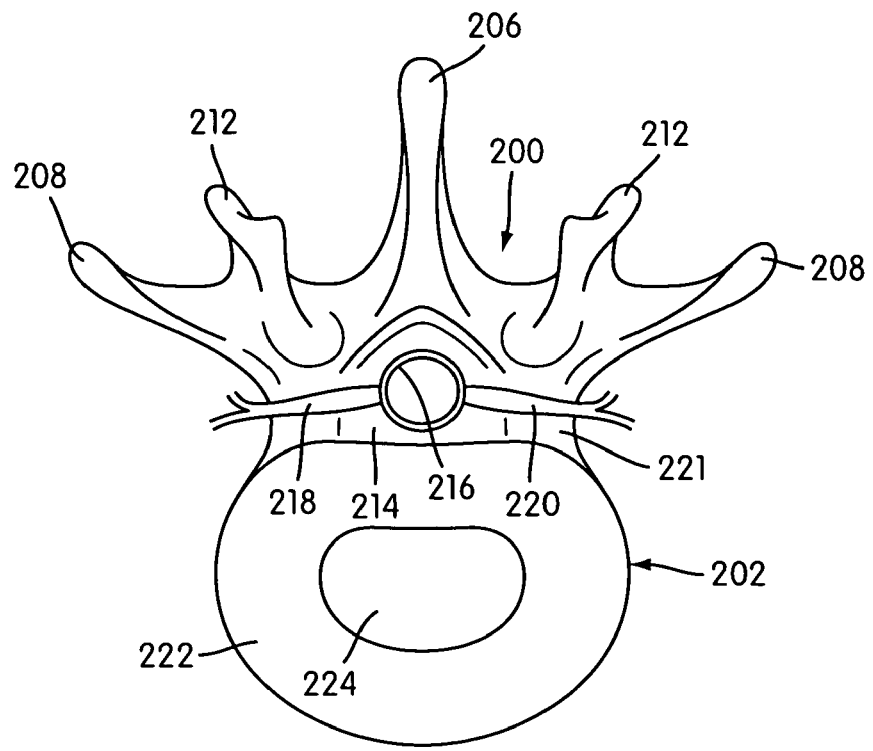
FIG. 1 is a plan view of a single vertebra and its associated intervertebral disc, illustrating the relevant anatomical structures.
Figure 2:
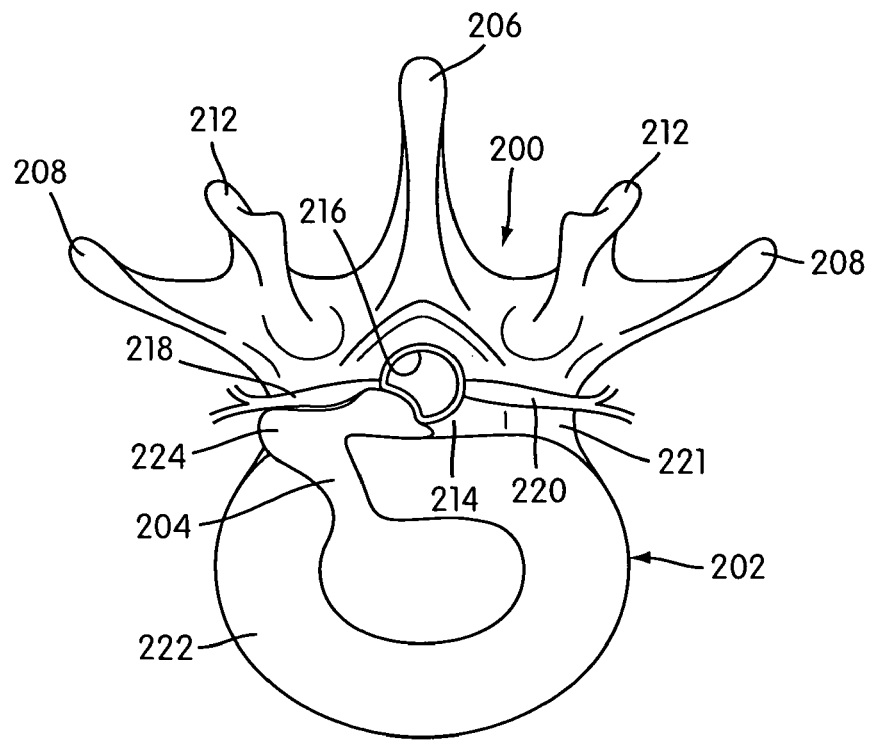
FIG. 2 is a plan view similar to that of FIG. 1, illustrating a herniated or traumatized intervertebral disc.
Figure 3:
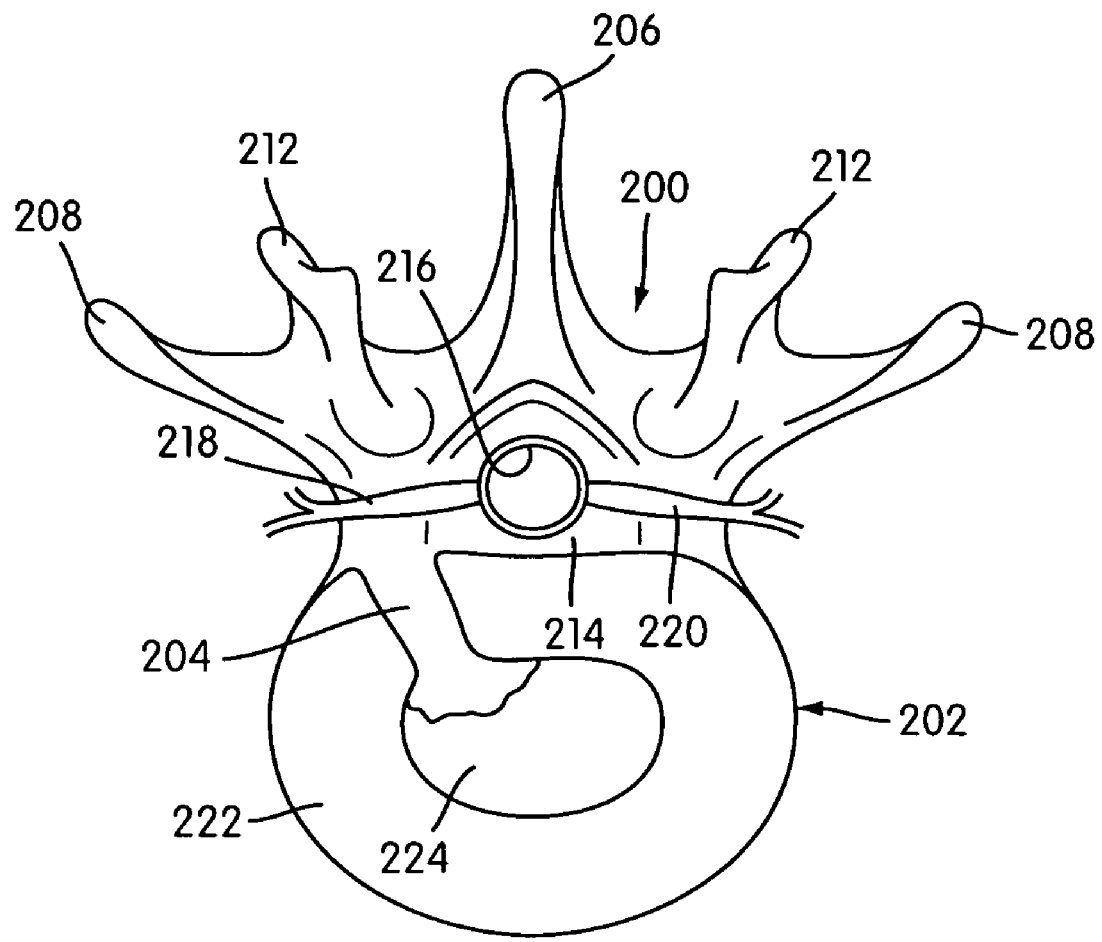
FIG. 3 is a plan view similar to that of FIG. 1, illustrating a herniated or traumatized disc after removal of nucleus pulposus material.
Figure 4:
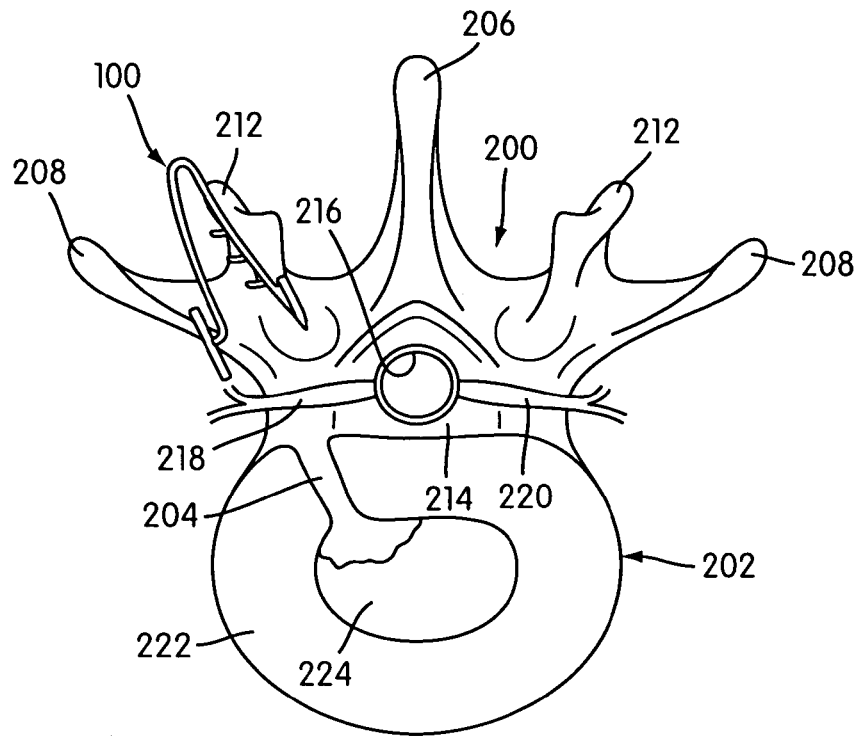
FIG. 4 is a plan view of a single vertebra and an associated intervertebral disc having a cut, tear, incision, hole or flaw, illustrating a closure prosthesis according to an embodiment of the invention in association with the intervertebral disc.
Figure 5:
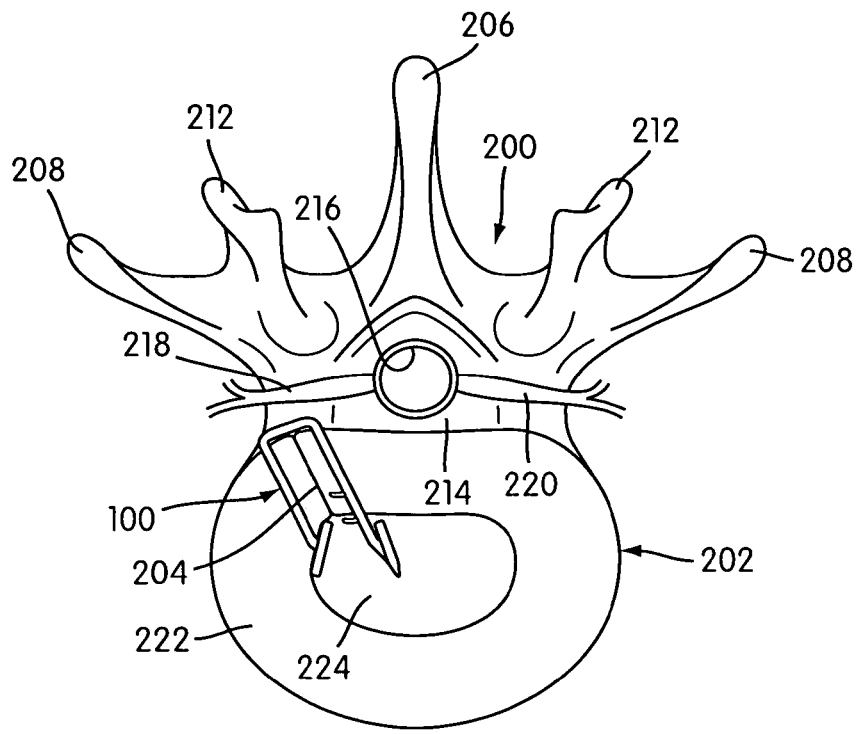
FIG. 5 is a plan view similar to that of FIG. 4, illustrating the closure prosthesis in position within the intervertebral disc to close the cut, tear, incision, hole, or flaw in the intervertebral disc.
Figure 6:
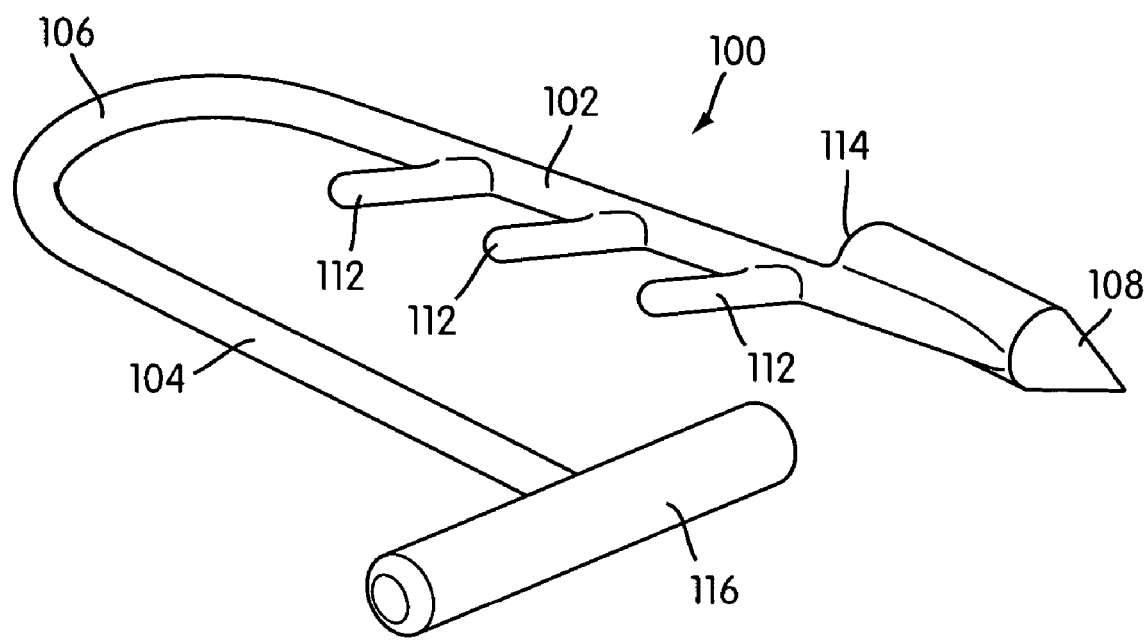
FIG. 6 is a perspective view of the closure prosthesis of FIGS. 4 and 5.

FIGS. 4-6 illustrate one embodiment of a closure prosthesis 100 that is adapted to close a flaw, imperfection, cut, incision, hole, or tear in an intervertebral disc 202. Specifically, FIGS. 4 and 5 are plan views of a single vertebra 200 and its associated intervertebral disc 202, illustrating the association of the closure prosthesis 100 with an intervertebral disc 202, and FIG. 6 is a perspective view illustrating the closure prosthesis 100 in isolation.

Although one particular embodiment of the closure prosthesis 100 is illustrated in those figures, the size, shape, and other characteristics of the closure prosthesis 100 may be determined based on a number of factors, potentially including the size and shape of the imperfection; the condition and type of tissue into which the closure prosthesis 100 is to be deployed; and the type and amount of circumferential or other stress that is to be exerted by the closure prosthesis 100 on the surrounding tissue. Recall that the term "imperfection" refers to any irregularity including a flaw, hole, tear, bulge, or, in some cases, a deliberate cut or incision.

The closure prosthesis 100 of FIGS. 4-6 has first and second portions 102, 104 with a connecting central portion 106 between first portion 102 and second portion 104. As shown in FIGS. 4 and 5, closure prosthesis 100 is adapted to be associated with an intervertebral disc 202 such that its first and second portions 102, 104 are arranged on either side of the cut or incision 204 in the disc 202. Some embodiments include provisions for closing the cut or incision 204. Once in place, closure prosthesis 100 can apply a circumferential hoop stress to the intervertebral disc 202 proximate the cut or incision 204 and can improve the axial loading characteristics of the intervertebral disc 202. Closure prosthesis 100, by cinching together intervertebral disc 204, may also increase the axial height of the disc.

The first portion 102 of the closure prosthesis 100 has a relatively pointed end 108 that extends generally away from central portion 106. Along the length of the first portion 102 behind the pointed end 108 are number of projections 112 that extend inwardly and rearwardly, such that their free ends generally point toward central portion 106 of closure prosthesis 100. Although only a few projections 112 are shown in FIG. 6, the closure prosthesis 100 may include any number of projections 112, arranged over all or part of the closure prosthesis 100, including both first and second portions 102, 104 and connecting portion 106. Projections 112 can also be arranged in different planes.

Depending on the particular characteristics of pointed end 108, the pointed end 108 may also anchor the closure prosthesis 100. For example, the relatively larger back portion 114 of the pointed end 108 may also help to anchor the first portion 102 of closure prosthesis 100.

The second portion 104 of closure prosthesis 100 is relatively smooth along its length and includes an end 116 that extends substantially transversely to the second portion 104. For ease and clarity in description, the first and second portions 102, 104 may be referred to as "barbed portion 102" and "T-portion 104," which should be understood as being equivalent in meaning to the first and second portions 102, 104, respectively.

Central portion 106 of closure prosthesis 100 extends between first end portion 102 and second end portion 104 and connects first end portion 102 with second end portion 104. In some embodiments, central portion 106 is generally arcuate in shape with a generally circular cross-section, as shown in the embodiment of FIG. 6, although central portion 106 may also be any other shape (e.g., more rectangular, more oval, or more flat in cross-section) in other embodiments.

Closure prosthesis 100 may be made of a variety of materials, although it may be preferable to make the closure prosthesis 100 using a biocompatible material that is sufficiently rigid to hold a cut or incision in an intervertebral disc closed, yet sufficiently compliant so as to avoid further damaging the intervertebral disc should slight relative motion between the disc and closure prosthesis 100 occur. Examples of suitable materials include nylon, prolene, dacron, ultra high molecular weight polyethylene (UHMWPE), and other suitable suture materials.

In some embodiments, the closure prosthesis 100 may be formed of a bioabsorbable polymer that is gradually absorbed by the body. Some examples of suitable bioabsorbable materials are: poly L-lactic acid (PLLA), polyglycolic acid (PGA). Closure prosthesis can also be formed of other possible materials, including polytetrafluorethylene (PTFE), polyaryletherketone (PAEK), polyetheretherketone (PEEK), polyoxymethylene (acetal), polycarbonate, polysulfone, silicone elastomers, commercially pure titanium, titanium alloys, CoCr alloys, nickel titanium (nitinol) alloys and implant grade stainless steels.

The closure prosthesis 100 may be made in a variety of shapes, as appropriate for different size incisions, cuts, and holes. These holes can vary from about 3-4 mm to 3-4 cm. Additionally, although FIG. 6 illustrates an embodiment of the closure prosthesis 100 in which both the barbed portion 102 and the T-portion 104 are of roughly equal size, one portion 102, 104 may be relatively enlarged with respect to the other portions. For example, it may be desirable to make one end portion 102, 104 larger if needed to provide better anchoring to close a larger cut, or a cut of a particular shape. Additional embodiments of the closure prosthesis will be described below with respect to FIGS. 37 and 38.

A user may install closure prosthesis 100 during a surgical procedure to repair intervertebral disc damage by manually inserting it, with or without the help of additional tools, as shown in FIGS. 4 and 5. However, a deployment device may also be used to install closure prosthesis 100. Closure prosthesis 100 can also be used to repair tendons, muscles, fascia, bone, cartilage, meniscus, ligaments or skin.

Figure 7:
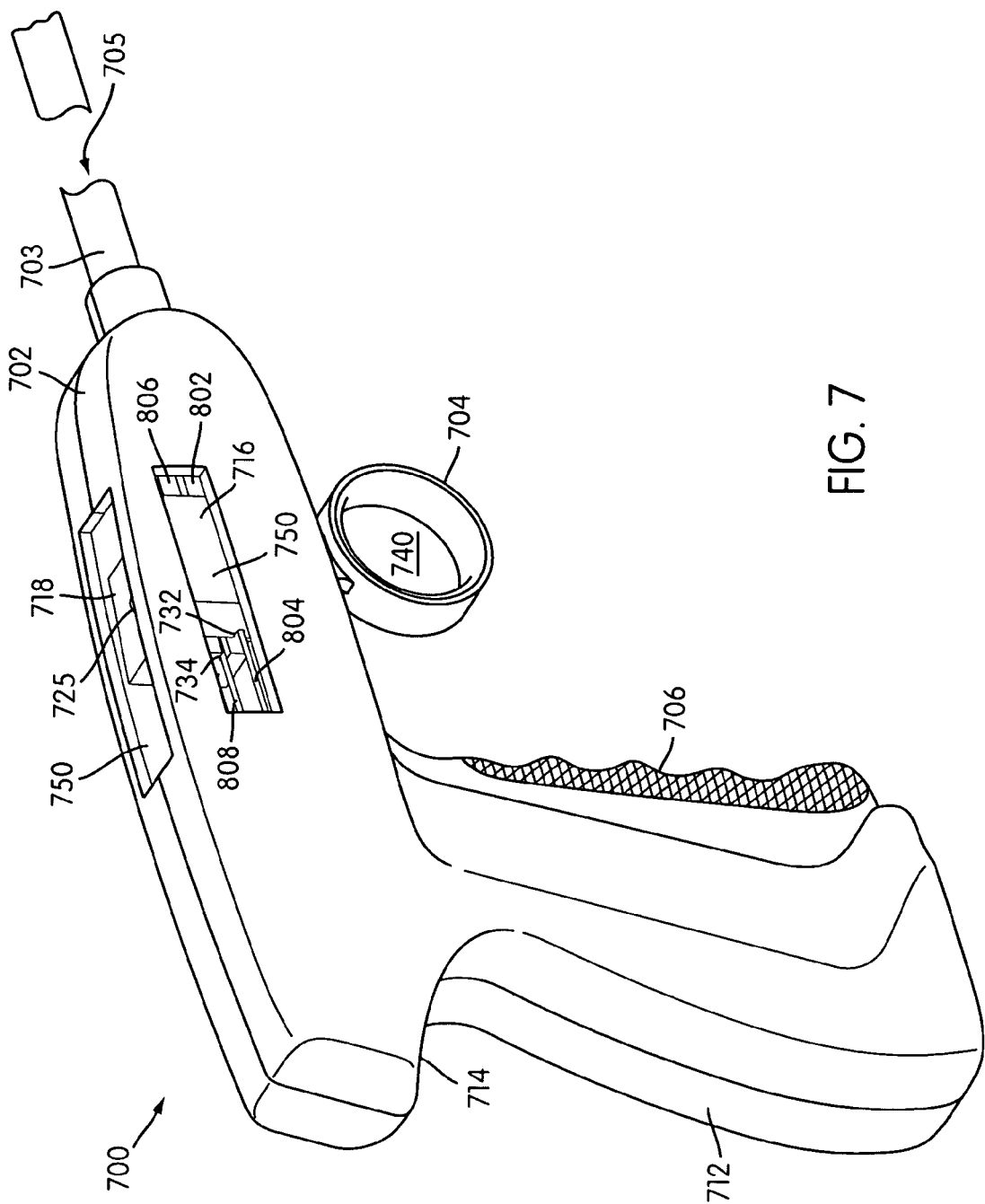
FIG. 7 is a perspective view of one embodiment of a deployment device that may be used to deploy the closure prosthesis of FIG. 4-6.

FIG. 7 is a perspective view of one embodiment of a deployment device 700 that is adapted to install closure prosthesis 100. Deployment device 700 in combination with prosthesis 100 may be referred to as a system. Deployment device 700 includes a body that contains a number of elements that assist in inserting and installing closure prosthesis 100. Preferably, deployment device 700 includes provisions to move closure prosthesis 100 into position, and provisions that associate one or more end portions of closure prosthesis 100 with disc 202. In some embodiments, deployment device 700 is configured for one-handed operation so that all of the various functions can be controlled with one hand and closure prosthesis 100 can be associated with disc 202 using a single hand.

In an exemplary embodiment, the distal end of body 702 is coupled to a canula 703. The lumen 705 of the canula 703 can be configured to carry closure prosthesis 100, along with provisions that help to insert and install it. The installation of closure prosthesis 100 and its arrangement within the lumen 705 of the canula 703 will be described in greater detail below. The body 702 can include a number of windows or cutouts 750 that allow a user to verify the position of the components that install closure prosthesis 100.

Preferably, the provisions in the deployment device 700 for inserting and/or deploying closure prosthesis 100 include provisions for moving or advancing one or both of barbed portion 102 and T-portion 104 of the closure prosthesis 100, either simultaneously or differentially, so as to cause closure prosthesis 100 to span a cut, tear, hole, incision or flaw 204.

Figure 8:
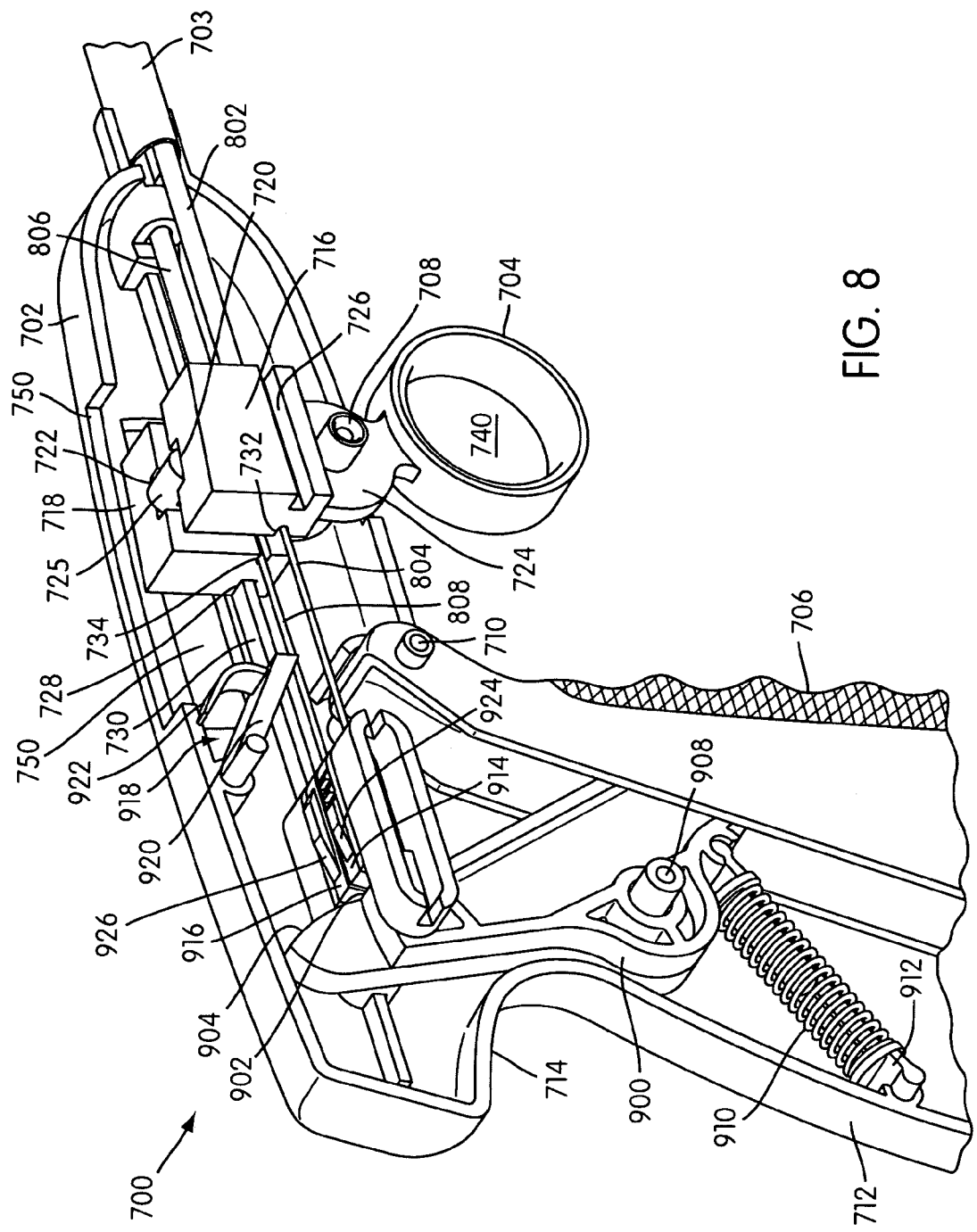
FIG. 8 is a cut-away perspective view of the device of FIG. 7 illustrating its components.

FIG. 8 is a cut-away perspective view of one embodiment of deployment device 700, illustrating its components. The deployment device 700 includes a first trigger 704 and a second trigger 706. In the embodiment of FIG. 8, first trigger 704 is attached to body 702 via first pivot pin 708. Pivot pin 708 allows the first trigger 704 to pivot or rotate relative to the body 702. The second trigger 706 is also designed to pivot or rotate relative to body 702. As shown, the second trigger 706 is coupled to the body 702 via a second pivot pin 710. Given this configuration, the second trigger 706 rotates about the body 702 at the second pivot pin 710.

The deployment device 700 is designed to be easily held, handled and used by a user. To that end, the deployment device 700 includes a handgrip portion 712 and a thumbrest 714. The handgrip portion 712 and the thumbrest 714 are designed to accommodate either the left or right hand of a user. In some cases, a user's hand might engage the handgrip portion 712 and use the palm and fingers to move or actuate the second trigger 706. One of the user's fingers can be used to actuate or move the first trigger 704. In the embodiment of FIG. 8, first trigger 704 is designed as a loop and includes a hole 740, although other configurations are possible and may be used to improve the ergonomics or user comfort of the deployment device 700. Preferably, first trigger 704 operates independently from second trigger 706. As shown, the handgrip portion 712, the first and second triggers 704, 706, and any other portion of the body may be knurled or otherwise surface-modified to improve grip or traction. A variety of different materials, coatings and/or surface treatments can be used on either or both triggers to improve grip and prevent slipping.

Preferably, the provisions for moving or advancing one or both of barbed portion 102 and T-portion 104 of the closure prosthesis are provisions that convert the rotational/pivotal movement of the first trigger 704 and/or the second trigger 706 into linear motion that results in the deployment of closure prosthesis 100. In some embodiments, the provisions for moving or advancing barbed portion 102 and T-portion 104 may move or advance those portions in one-to-one correspondence with the amount of motion or pressure imparted to the first and second triggers 704, 706 by the user. However, in other embodiments, the coupling between the first and second triggers 704, 706 may be more indirect, and the motion of barbed portion 102 and T-portion 104 may not have a direct, one-to-one correspondence with the forces or motions applied to the first and second triggers 704, 706. More indirect coupling of the movement of the first and second triggers 704, 706 and the movement of barbed portion 102 and T-portion 104 may help to produce a smooth advancement, insertion, and/or placement of closure prosthesis 100 even if the force or movement applied to the first and second triggers 704, 706 by the user is not itself smooth.

Figure 12:
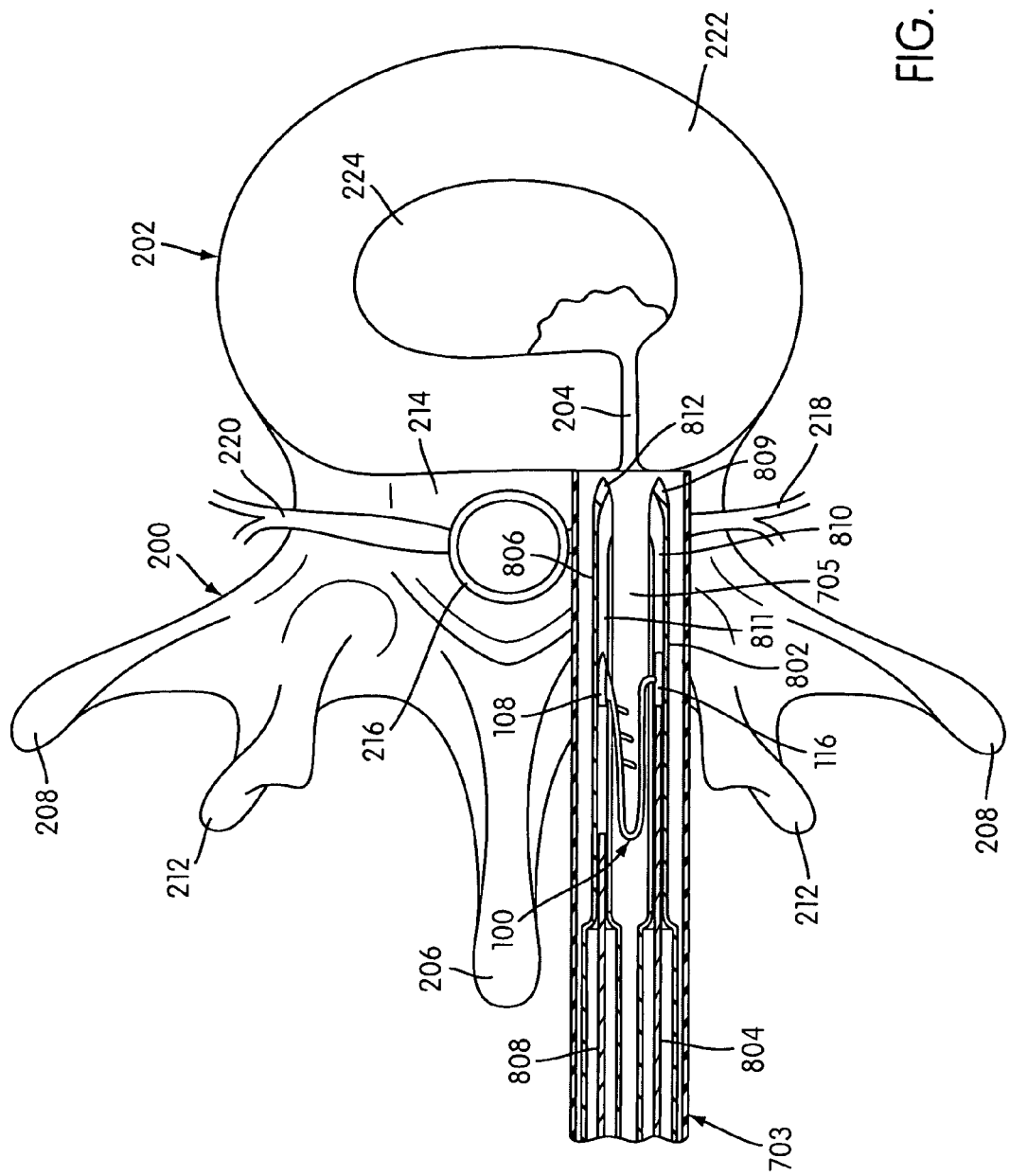
FIG. 12 is a sectional view of a vertebral column, illustrating a vertebra associated with a cut intervertebral disc, and showing one end of the deployment device of FIG. 7 in cross-section, positioned to install the closure prosthesis of FIG. 6.

The components and functions of the deployment device 700 are better understood with reference to FIG. 12, a sectional view of a vertebra 200 associated with an intervertebral disc 202, showing one end of the deployment device 700 in section, positioned to install closure prosthesis 100. In the embodiment shown in FIG. 12, the intervertebral disc 202 has a cut 204 facing dorsally, and the user has inserted the canula 703 of the deployment device 700 past the spinous, transverse, and mammillary processes and facet joints 206, 208, 212 of vertebra 200 to reach a location proximate to cut 204. Canula 703 may be of any length necessary to achieve proper positioning for installation of closure prosthesis 100. Additionally, although the features and proportions shown in FIG. 12 and in other figures are those of human anatomy, closure prosthesis 100 and deployment device 700 may be used on any mammal.

As shown in FIGS. 7 and 12, the lumen 705 of canula 703 contains first and second penetrating members 802, 806. Preferably, first penetrating member 802 is configured to retain one end portion of closure prosthesis 100 and second penetrating member 806 is configured to retain the other end portion of closure prosthesis 100 prior to deployment. In some embodiments, first and second penetrating members 802 and 806 are generally hollow with forward penetrating tips 809 and 812, repsectively. In some embodiments, forward penetrating tips 809 and 812 are designed to act as cutting needles, tapered needles or any other suitable needle design. Preferably, each penetrating member 802, 806 has an open channel 810, 811 formed along its inner face and an associated hole. Although the preferred embodiment includes holes oriented inwards, the holes can be oriented in other directions as well.

Closure prosthesis 100 is preferably mounted so that the pointed end 108 is disposed within the second penetrating member 806, and portions of barbed portion 102 protrude out of second channel 811. Preferably, transverse end 116 is within the first penetrating member 802, and the barbed portion 102 and the T-portion 104 extend out of the respective channels 810, 811 in the penetrating members 802, 806 such that the central connecting portion 106 extends between the two penetrating members 802, 806. First and second push rods 804, 808 are also arranged within the first and second penetrating members 802, 806.

In some embodiments, first push rod 804 is slightly longer than the second push rod 808, such that in the view of FIG. 12, before the deployment device 700 is actuated to deploy the closure prosthesis 100, first push rod 804 extends farther than the second push rod 808 and can be in contact with the transverse end 116. In some embodiments, the distal end of the second push rod 808 is initially positioned some distance back from the barbed portion 102. The push rods 804, 808 are generally coaxial with penetrating members 802, 806.

As will be explained below in greater detail, in one embodiment, actuation of the first trigger 704 forces the penetrating members 802, 806 into the intervertebral disc 202 proximate to the cut 204. Actuation of the second trigger 706 causes the push rods 804, 808 to force the prosthesis 100 out of the penetrating members 802, 806 and into position in the intervertebral disc 202.

In this embodiment, the length differential of the first and second push rods 804, 808, in combination with other features and provisions in deployment device 700, typically causes the T-portion 104 to be deployed before the barbed portion 102, although this need not be the case in all embodiments. This will be explained below in greater detail.

The opposite ends of the penetrating members 802, 806 and the push rods 804, 808 extend rearwardly through the lumen 705 of the canula 703 and are received in the body 702 of deployment device 700, as shown in FIG. 8. The first and second penetrating members 802, 806 terminate at and are coupled to respective first and second penetration member actuators 716, 718. The penetration actuators 716, 718 can be generally rectangular blocks that are slidably mounted within body 702. Preferably, each of the first and second penetration actuators 716, 718 includes a guide groove 726, 728 formed in an outward face of the penetration actuator 716, 718. A guide rib 730 fixed with respect to body 702 is received in each of the guide grooves 726, 728. This arrangement helps to secure each of the penetration actuators 716, 718 to body 702 and also allow for sliding movement along the guide ribs 730. In FIG. 8, only the guide rib 730 associated with the second actuator 718 is shown; another guide rib (not shown) engages first actuator 716 in a same manner. The first and second penetration actuators 716, 718 may be made of a plastic or of another material with a low coefficient of sliding friction in order to minimize both wear and resistance to movement.

Each of the first and second actuators 716, 718 also includes a main groove 720, 722. Preferably, main groove 720, 722 is disposed on a face opposite from guide groove 726, 728. In operation, the actuators 716, 718 are positioned in alignment with each other, as shown in FIG. 8, and a single push member 724 coupled to first trigger 704 is received in main grooves 720, 722. By engaging main grooves 720, 722, push member 724 is able to drive actuators 716, 718 in simultaneous sliding movement along the respective guide ribs 730. Because the push member 724 is coupled to the first trigger 704, a pivotal rearward movement of the first trigger 704 about the pivot pin 708 (clockwise rotation in FIG. 8) causes a simultaneous and coinciding forward movement of the actuators 716, 718 in the distal direction, thereby forcing the respective penetrating members 802, 806 forward. In some embodiments, the push member 724 and the first trigger 704 may be formed integrally.

Figure 19:
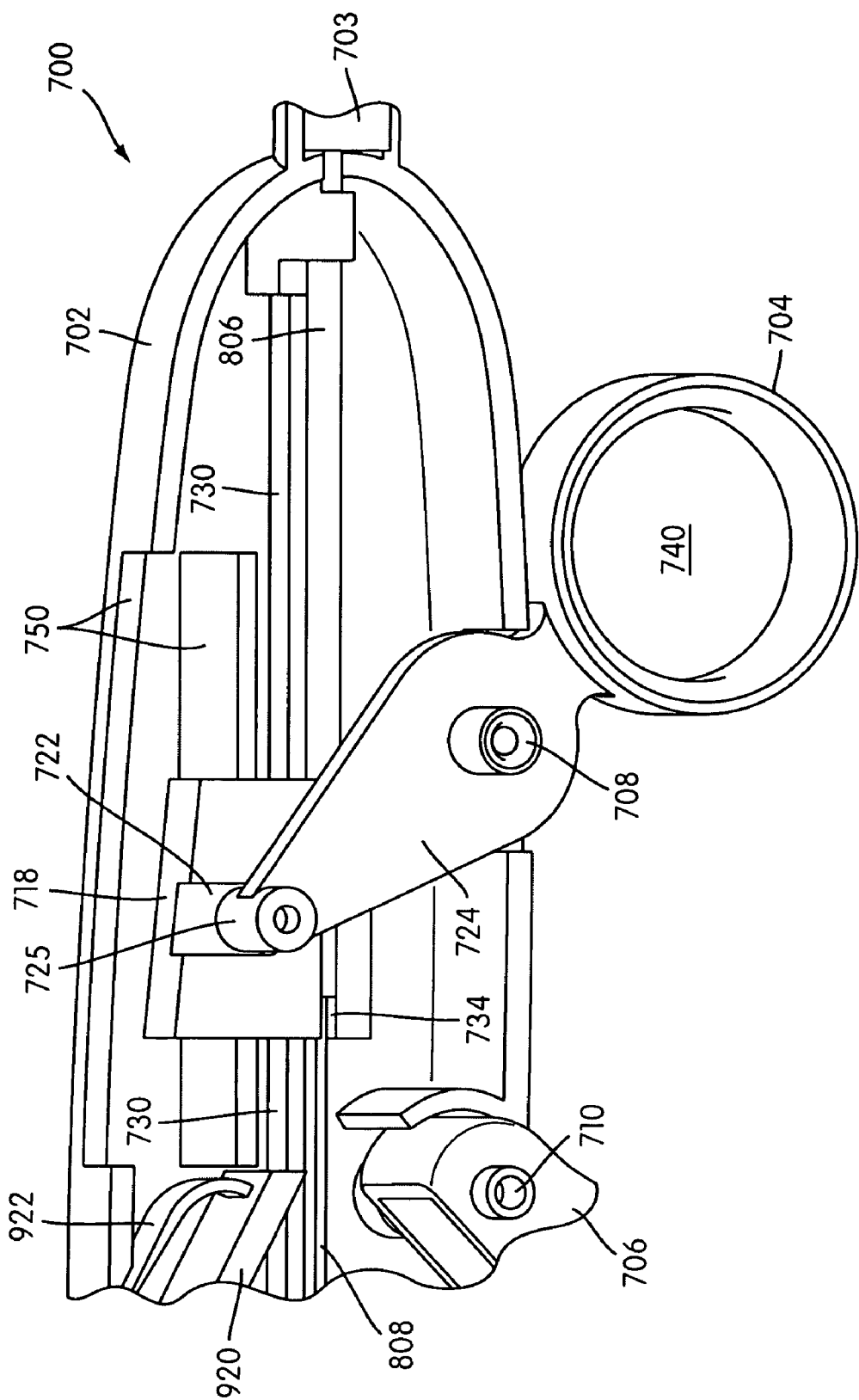
FIGS. 19-21 are partial perspective views of the forward end of the deployment device, illustrating the attachment of the first trigger mechanism to its associated components in a sequence of operational positions.
Figure 20:
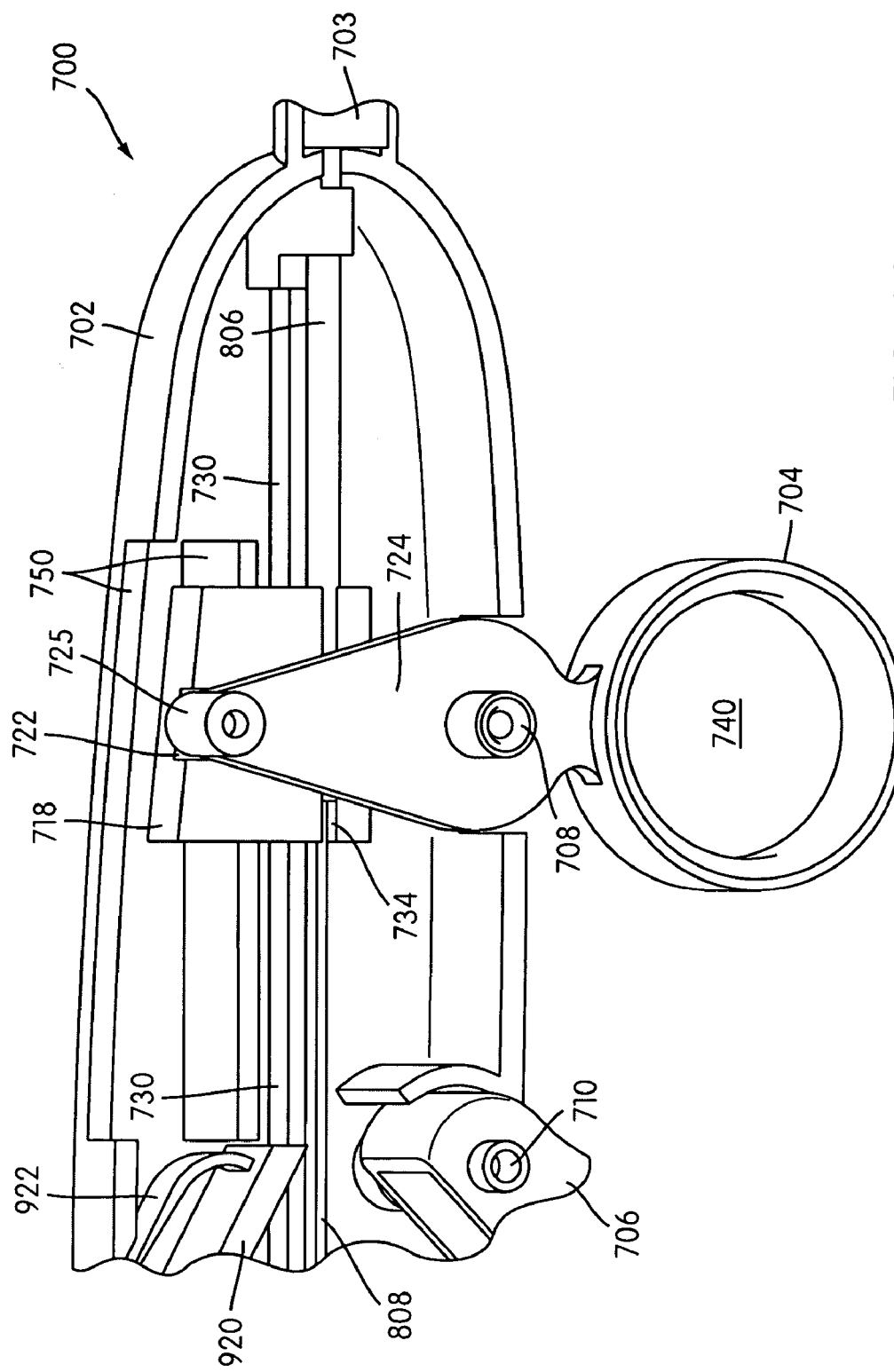
Figure 21:
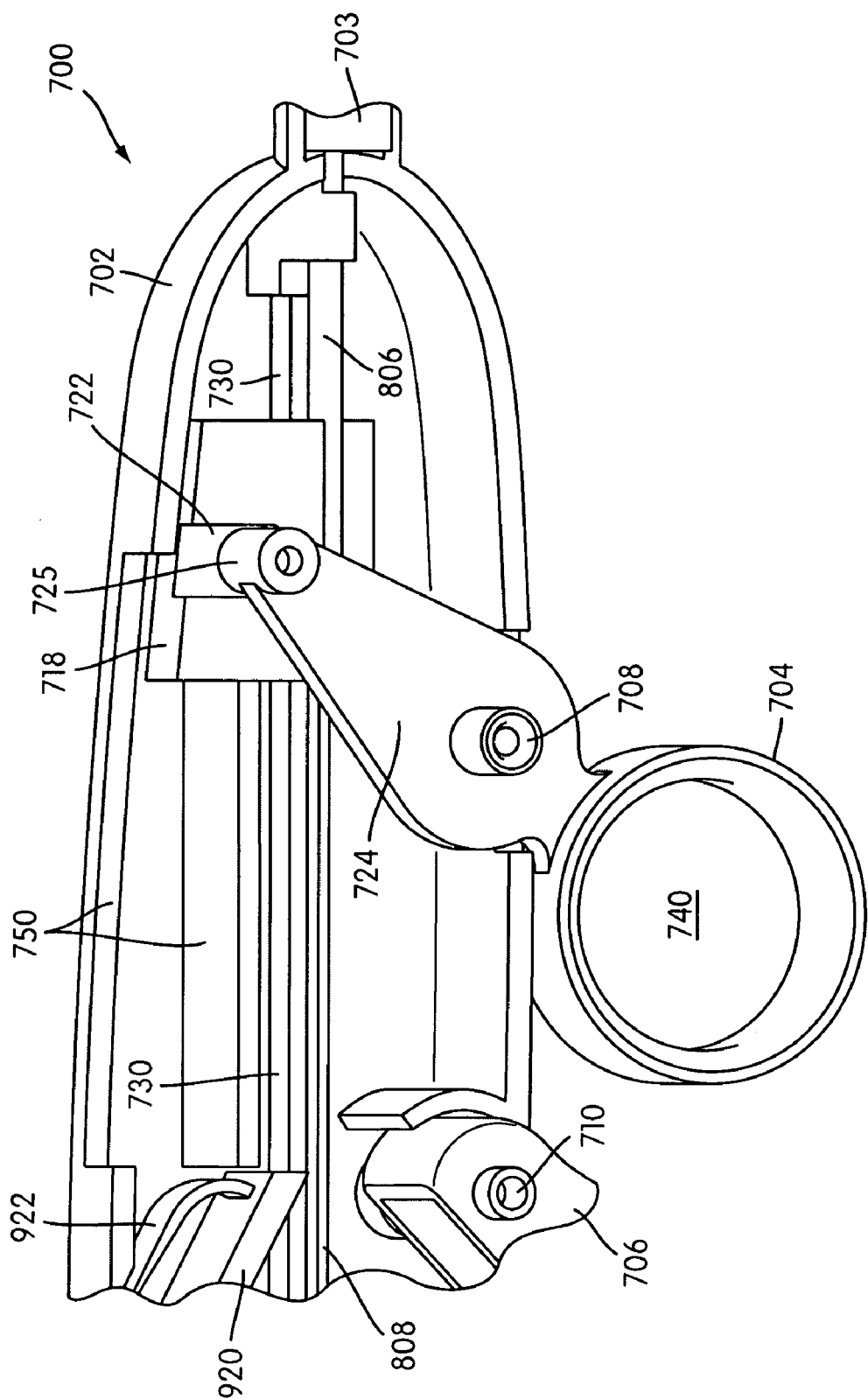
Figure 22:
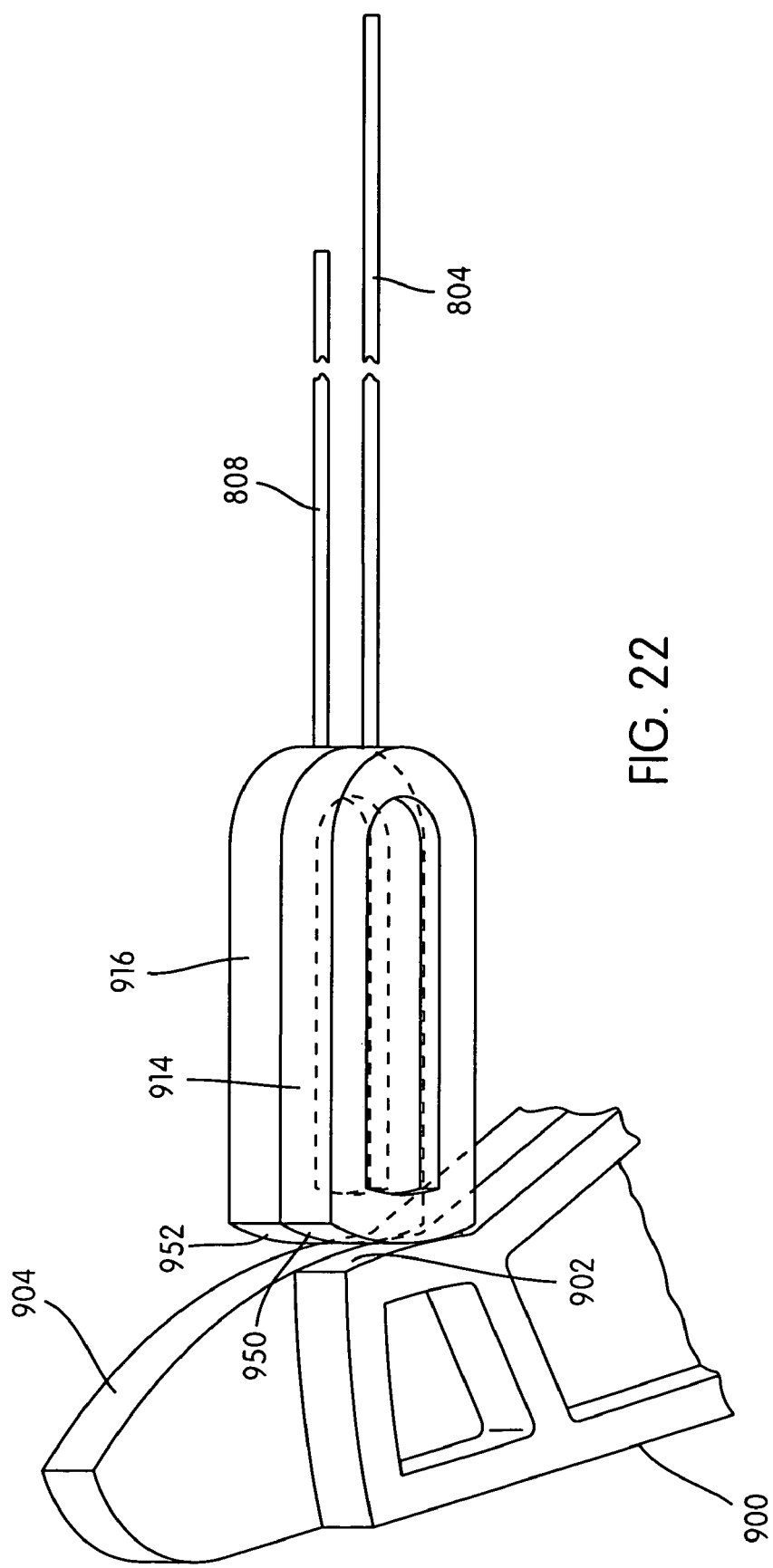
FIGS. 22-25 are perspective views illustrating the cams and followers associated with the second trigger mechanism in isolation, showing the sequence of motion in the cams and followers following actuation of the second trigger mechanism and illustrating schematically the positions of the ends of push rods coupled to the followers.

FIGS. 19-21 are cut-away perspective views of the forward end of deployment device 700, illustrating the manner of engagement of the push member 724 and the main grooves 720, 722 in various operational positions. Although only main groove 722 is shown in FIGS. 19-21, the motion and manner of engagement may be assumed to be identical for the other main groove 720. As shown, the push member 724 terminates in a slider 725 that moves within main groove 722 of actuator 718. In the forward-most position of the first trigger 704, illustrated in FIG. 19, the slider 725 is located substantially at the bottom of the main groove 722. At this trigger position, actuator 718 is at a rearward or proximal position.

In the midway-rotated position of the first trigger 704, illustrated in FIG. 20 (and also in FIG. 8), the slider 725 has reached the top of the main groove 722. At this midway-rotated trigger position, actuator 718 is at a middle or intermediate position. In the fully-rotated position of the first trigger 704, illustrated in FIG. 21, the slider 725 is once again at the bottom of the main groove 722. At this fully rotated trigger position, actuator 718 is at a forward or distal position. The illustrated series of movements of the slider 725 occurs because the push member 724 is rigidly coupled to the first trigger 704, and thus, the slider 725 travels in an arc as the first trigger 704 is rotated. This rotational motion is converted into linear motion by cooperation of push member 724 within main groove 722, and because guide rib 730 helps to limit the motion of actuator 718. In other embodiments, if the push member 724 is coupled to the first trigger 704 more indirectly (e.g., by a linkage), the structures, movements, and manner of engagement may be entirely different than those shown in FIGS. 19-21.

As shown in FIG. 8, the deployment device 700 preferably includes provisions to help deploy closure prosthesis 100. In some embodiments, deployment device 700 includes provisions to support and guide the movement of structures that advance and deploy the closure prosthesis 100. In the illustrated embodiment, the first and second push rods 804, 808 extend proximally (rearward as shown in FIG. 8) out of the penetrating members 802, 806 into body 702 of deployment device 700. Preferably, first and second push rods 804, 808 are received in and guided by first and second channels 732, 734 disposed in respective actuators 716, 718.

Preferably, the push rods 804, 808 move independently of the actuators 716, 718, and the first and second channels 732, 734 provide support for the push rods 804, 808 without influencing their axial movement while providing lateral guidance. Behind actuators 716, 718, first and second push rods 804, 808 terminate at and are attached to respective first and second sliding followers 914, 916. The followers 914, 916 are slidably mounted along the respective guide ribs 730 (the other guide rib is not shown in the Figures). Preferably, first and second sliding followers 914, 916, are coupled to second trigger 706, such that rearward motion of the second trigger 706 produces forward motion of the first and second followers 914, 916, causing the push rods 804, 808 to move forward, as will be explained below in greater detail.

Preferably, body 702 includes a coupling member 900 disposed behind second trigger 706. In some embodiments, coupling member 900 is a relatively elongate member that is mounted within the body 702 for rotation about a pivot pin 908 formed on the interior of handgrip portion 712. A linking member 912 is rotatively mounted, on one end, to the rear of the handgrip portion 712 and, at the other end, to coupling member 900. The end of the coupling member 900 in which the linking member 912 is received bears against the inside of the second trigger 706. A spring 910 is mounted over the linking member 912, such that the linking member 912 acts as a spring guide. With the arrangement of the coupling member 900, the linking member 912, and the spring 910, the second trigger 706 is biased forwardly when not depressed because of the force of the spring 910 acting through the coupling member 900 on the inside of the second trigger 706.

One end of the coupling member 900 preferably includes first and second cam surfaces 902, 904 that bear against respective first and second bearing surfaces 950, 952 associated with respective first and second followers 914, 916. Preferably, the shape and characteristics of the cam surfaces 902, 904 and, optionally, the bearing surfaces 950, 952 are adapted to produce a set of movements appropriate to deploy the closure prosthesis 100. The particular movements that the cam surfaces 902, 904 and the bearing surfaces 950, 952 are adapted to produce may vary with the application and with the type and characteristics of the closure prosthesis 100.

As shown in FIG. 8, the two cam surfaces 902, 904 are not identical, such that when the coupling member 900 is caused to rotate by relative movement of the second trigger 706, the movement produced in the first and second followers 914, 916 is not identical. Specifically, the first cam surface 902 is relatively shorter in height as compared with the second cam surface 904, such that the first cam surface 902 bears on the first bearing surface 950 early in the movement cycle and then moves to a position below the first follower 914. The specific movement sequence and potential advantages of the illustrated profiles of the first and second cam surfaces 902, 904 will be described below in more detail. However, in other embodiments, the two cam surfaces 902, 904 may be identical, resulting in initial identical, simultaneous movement of the two followers 914, 916.

The actual profiles of the two cam surfaces 902, 904 may be determined depending on the size of the prosthesis 100 and the amount of movement of one follower 914, 916 relative to the other follower 914, 916 that is desired, among other factors. The profiles illustrated in FIG. 8 are but one example.

The deployment device 700 preferably also includes provisions for temporarily fixing the position of one or more elements used to deploy closure prosthesis 100 during some or all of the deployment cycle. In the illustrated embodiment, the body 702 of the deployment device 700 includes a locking catch mechanism generally indicated at 918. The locking catch mechanism 918 comprises a generally flat, relatively wide engaging member 920 that is pivotally mounted along the top of the body 702 and extends downwardly, acting as a pawl. A leaf spring 922 attached to the upward face of the engaging member 920 bears against an upper inside surface of the body 702 and biases the engaging member 920 downwardly.

The first and second followers 914, 916 have respective engaging portions 924, 926 on their upward faces. Each of the first and second engaging portions 924, 926 is adapted to engage and cooperate with the engaging member 920 of the locking catch 918. As the followers 914, 916 move forward, the engaging portions 924, 926 are brought into contact with the engaging member 920. However, the manner in which the two engaging portions 924, 926 engage the engaging member 920 is different. Specifically, the first engaging portion 924 has engaging teeth that may lock it in place and prevent rearward movement with respect to the engaging member 920. The second engaging portion 926 is shaped such that it provides relatively free movement past the engaging member 920. As will be explained below in greater detail, the first engaging portion 924 may prevent the first follower 914 from moving rearwardly after the first cam surface 902 has moved to a downward position below the first follower 914 and can thus no longer prevent the first follower 914 from moving rearwardly.

Figure 9:
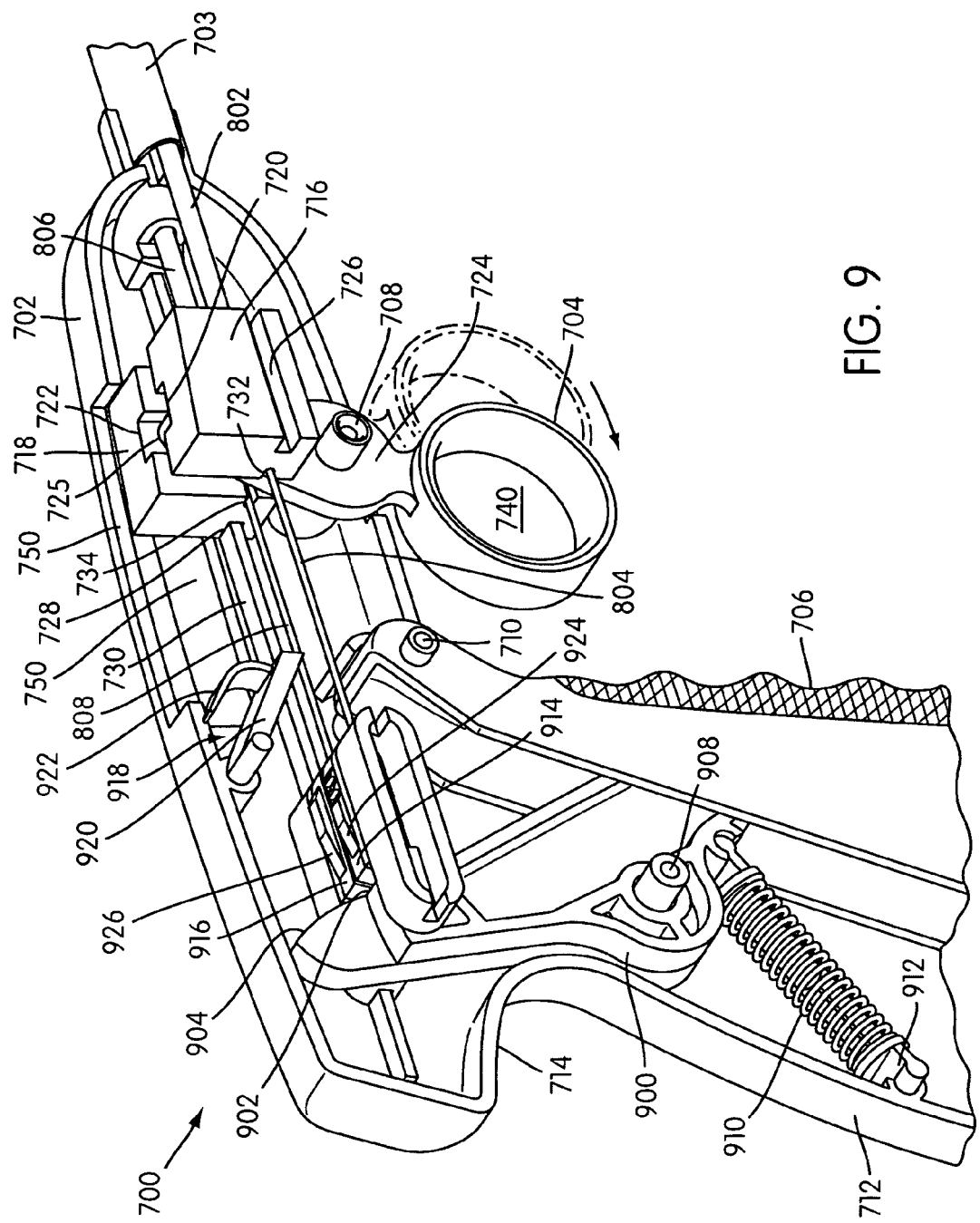
FIG. 9 is a cut-away perspective view similar to FIG. 8 showing the deployment device after actuation of a first trigger mechanism.
Figure 10:
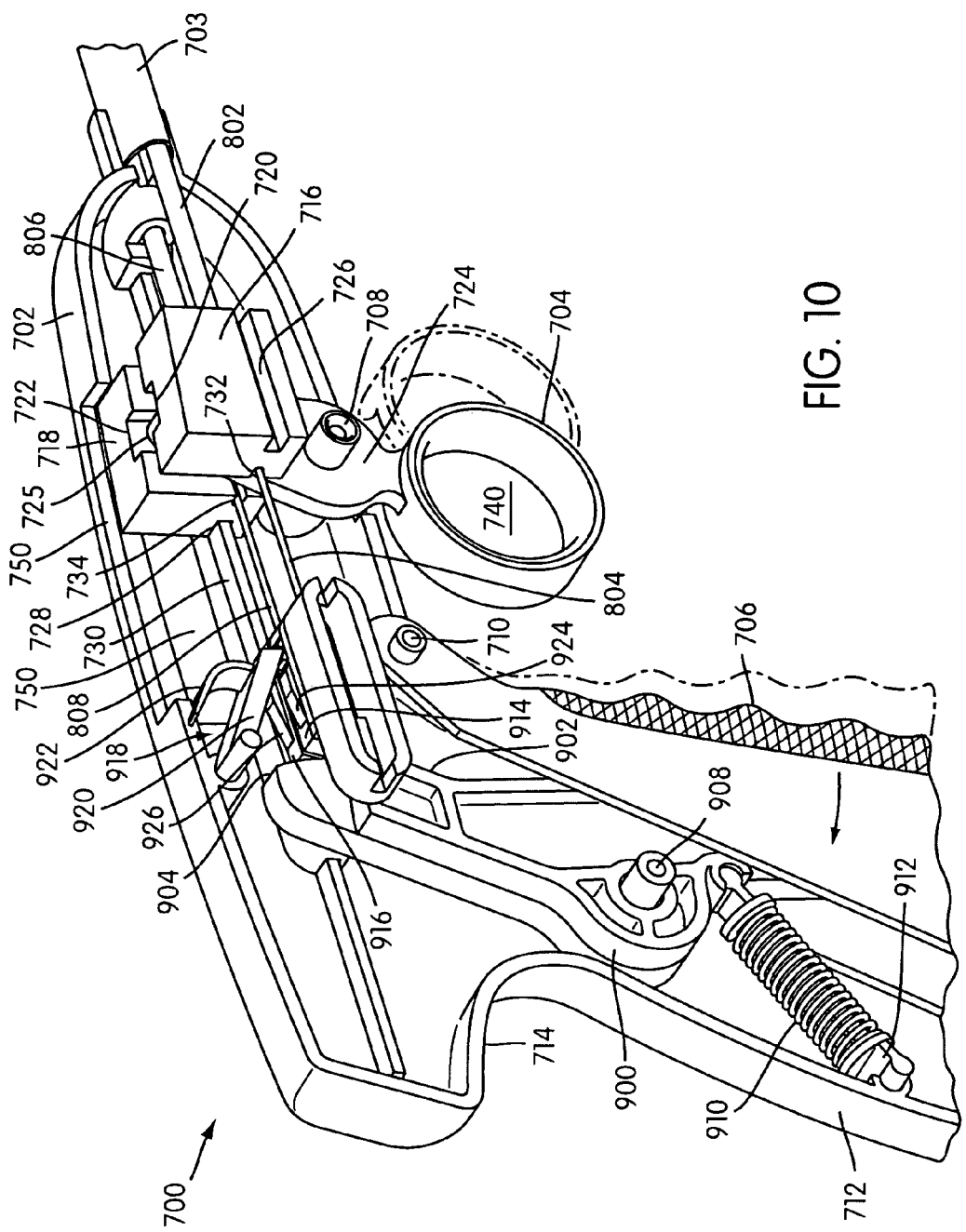
FIGS. 10 and 11 are cut-away perspective views similar to FIG. 8 showing the deployment device after actuation of a second trigger mechanism, illustrating a sequence of motions produced by the second trigger mechanism and its associated structures.
Figure 11:
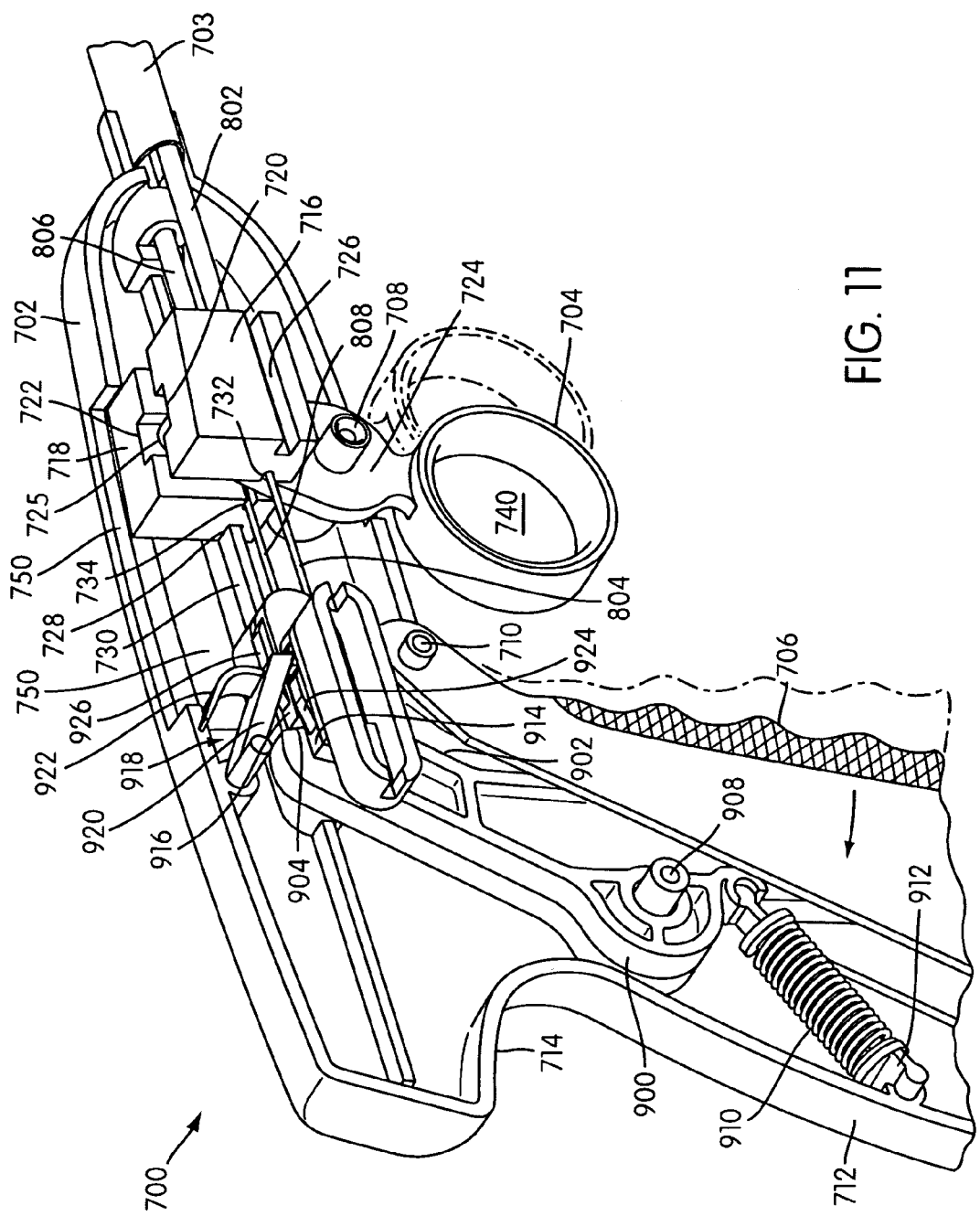

The interaction of the components described above and their relative motions are best understood with reference to FIGS. 9-11, which show the series of movements within the body 702 when the first and second triggers 704, 706 are actuated, and with respect to corresponding FIGS. 22-25, which are perspective views of the first and second cam surfaces 902, 904, the associated first and second followers 914, 916, and the push rods 804, 808 in isolation, illustrating the movements specific to those components as the second trigger 706 is actuated. In FIGS. 22-25, certain components have been omitted in order to focus on the first and second cam surfaces 902, 904 and the first and second followers 914, 916.

In the position shown in FIG. 9, as indicated by the arrow, the first trigger 704 has been pushed rearwardly, causing the push member 724 to move the actuators 716, 718 forward, which results in forward movement of the penetrating members 802, 806. In the position shown in FIG. 10, the first trigger 704 is still in its rearward, actuated position when the second trigger 706 is actuated and the coupling member 900 is caused to move such that the first and second cam surfaces 902, 904 and first and second followers 914, 916 move forward. In FIG. 10, the first and second followers 914, 916 have reached the position of cooperating with engaging member 920 and the engaging portion 924 of the first follower 914 engages the engaging member 920 to lock the first follower 914 in place. The second follower 916, because of its non-locking engaging portion 926, is free to continue moving forward as the second trigger 706 is actuated. As the motion continues, the second follower 916 continues moving forward until it reaches the position illustrated in FIG. 11.

Figure 23:
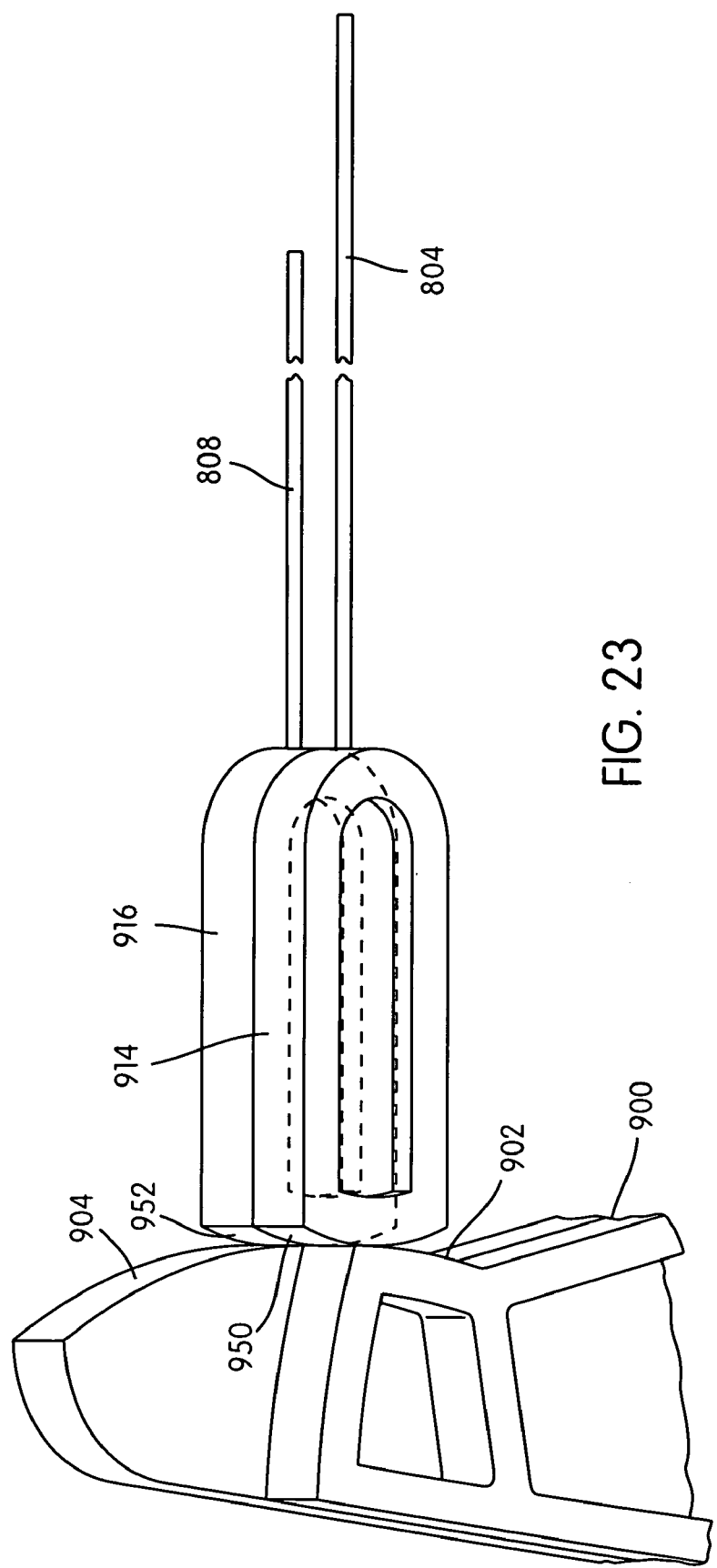
Figure 24:
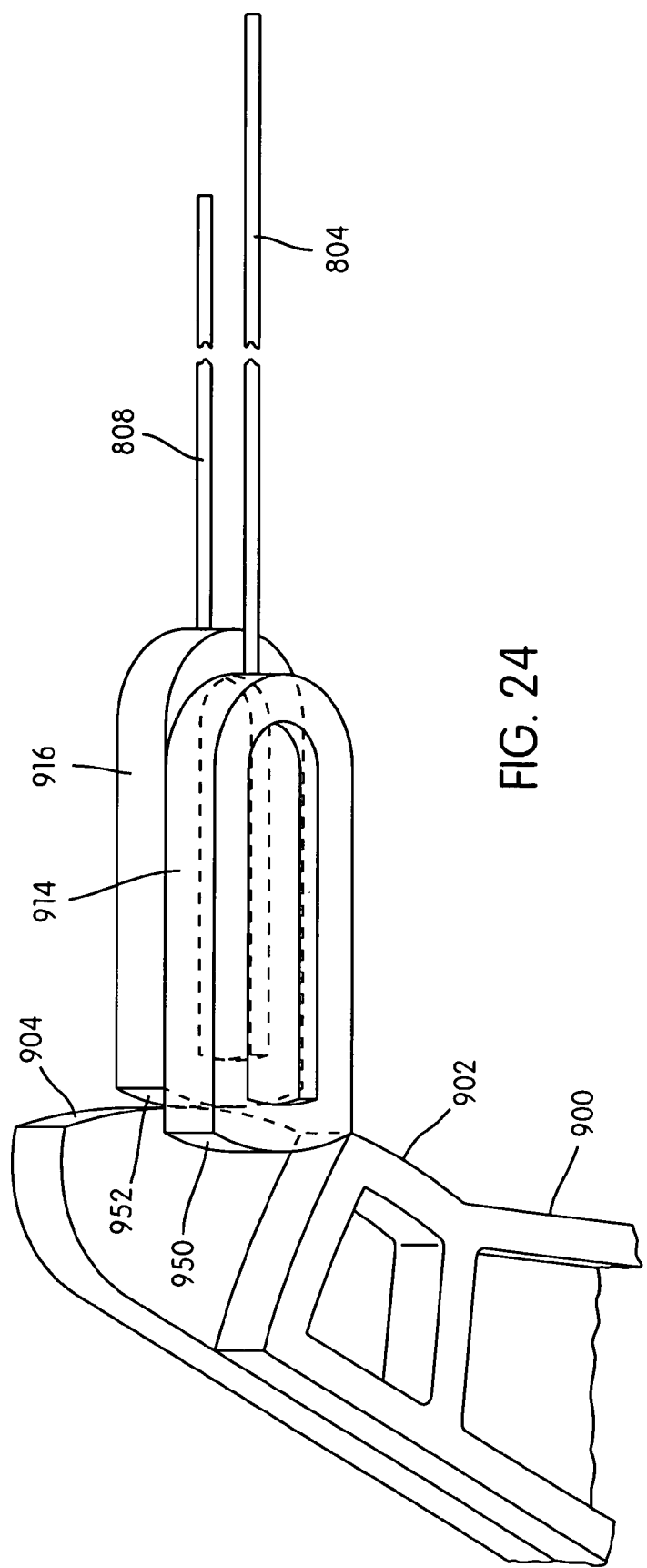
Figure 25:
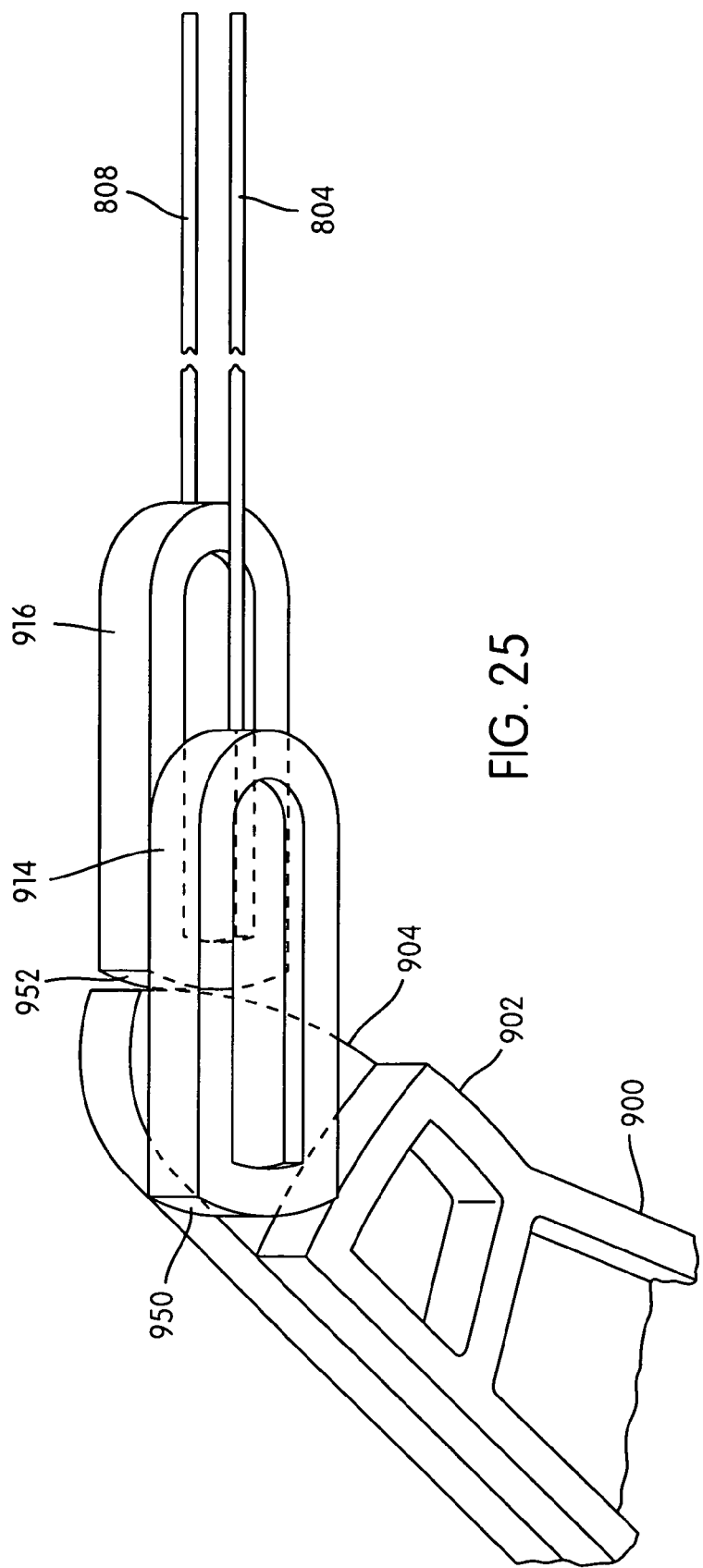

The interaction of the first and second cam surfaces 902, 904 with the first and second followers 914, 916 and the associated movements of the push rods 804, 808 can be seen more clearly in FIGS. 22-25. Of those figures, FIG. 22 corresponds to the initial position of the deployment device 700 prior to the actuation of the second trigger 706. FIG. 23 corresponds generally to the position shown in FIG. 10, and FIG. 24 corresponds to the position shown in FIG. 11. However, as will be readily appreciated, FIGS. 22-25 omit certain elements, such as the locking catch mechanism 918, in order to focus on the interaction of the first and second cam surfaces 902, 904 with the respective first and second followers 914, 916. FIG. 25 illustrates the full range of motion of the first and second followers 914, 916. In the position illustrated in FIG. 25, the first follower 914 is held in place by the action of the locking catch mechanism 918 acting upon it and can thus remain stationary in the illustrated position as the closure prosthesis begins to exert circumferential stress on the intervertebral disc 202. The action of the locking mechanism 918 prevents the T-portion 104 from being pulled rearwardly by the forces being applied by the second follower 916.

One other optional feature can be seen in FIGS. 22-25: the first and second bearing surfaces 950, 952 of the first and second followers 914, 916 are convexly curved. The curvature of the first and second bearing surfaces 950, 952 may allow for a smoother and more precise movement of the followers 914, 916, because of the smaller contact area between the first and second bearing surfaces 950, 952 and the respective first and second cam surfaces 902, 904. However, the shape of the first and second bearing surfaces 950, 952 need not be curved in all embodiments, and instead may be determined in accordance with the desired application and desired extent and nature of the movements to be generated.

Figure 13:
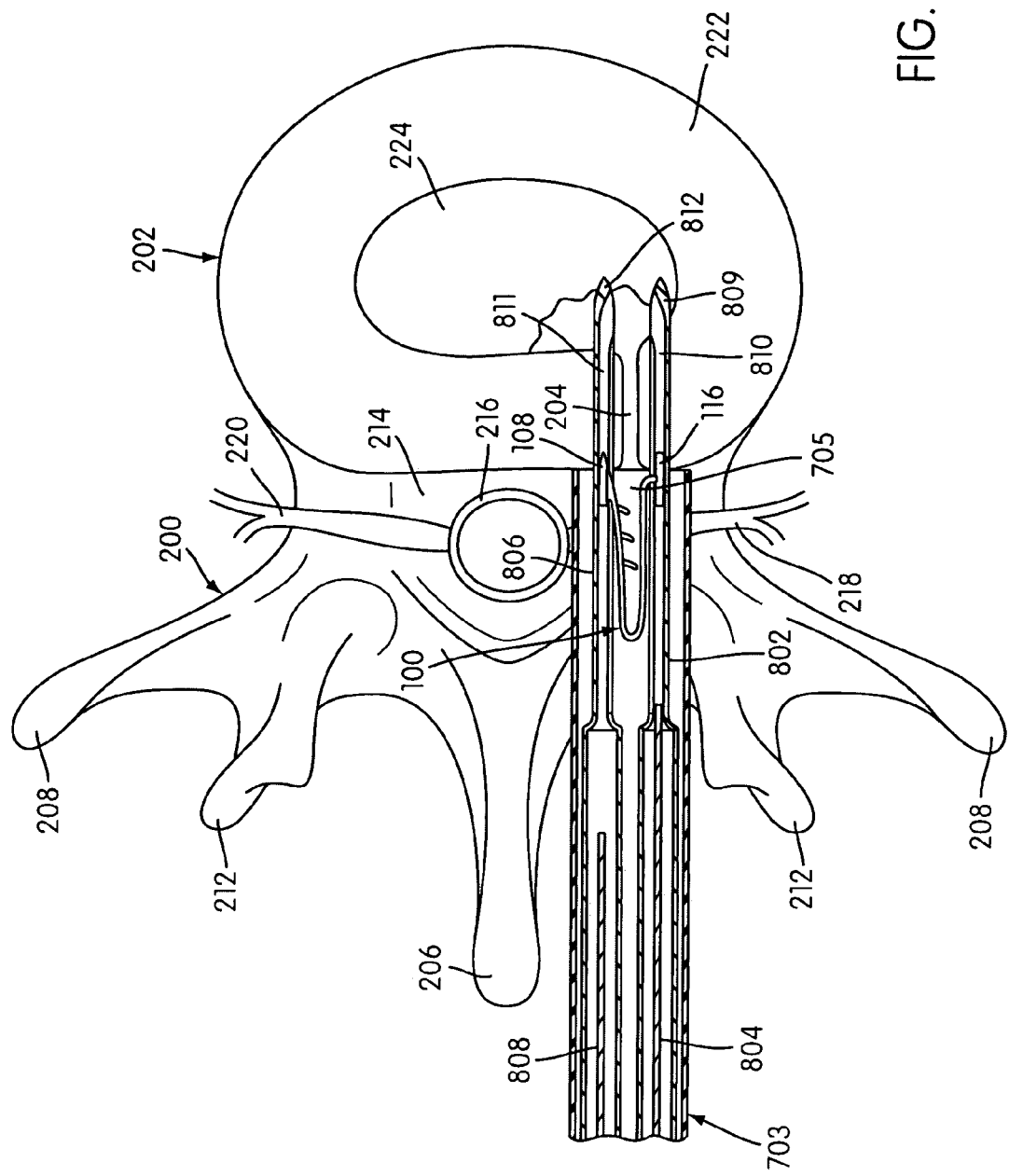
FIGS. 13-16 are sectional views similar to FIG. 12, illustrating the sequence of movements with which the closure prosthesis of FIG. 6 is installed.

FIGS. 8-11 and 22-25 primarily illustrate the movements of structures within the deployment device 700. The corresponding motion in canula 703 that installs the prosthesis 100 is illustrated in FIGS. 12-16. The initial position of the canula 703 in FIG. 12 (with neither one of the triggers 704, 706 depressed) was described above. In FIG. 13, the user has actuated the first trigger 704, causing the first and second penetrating members 802, 806 to penetrate the nucleus purposus 222 proximate to the cut 204. Once the first trigger 704 has been actuated and the penetrating members 802, 806 are in the position shown in FIG. 13, the user can then actuate second trigger 706, which, as was explained above, causes a series of movements.

Figure 14:
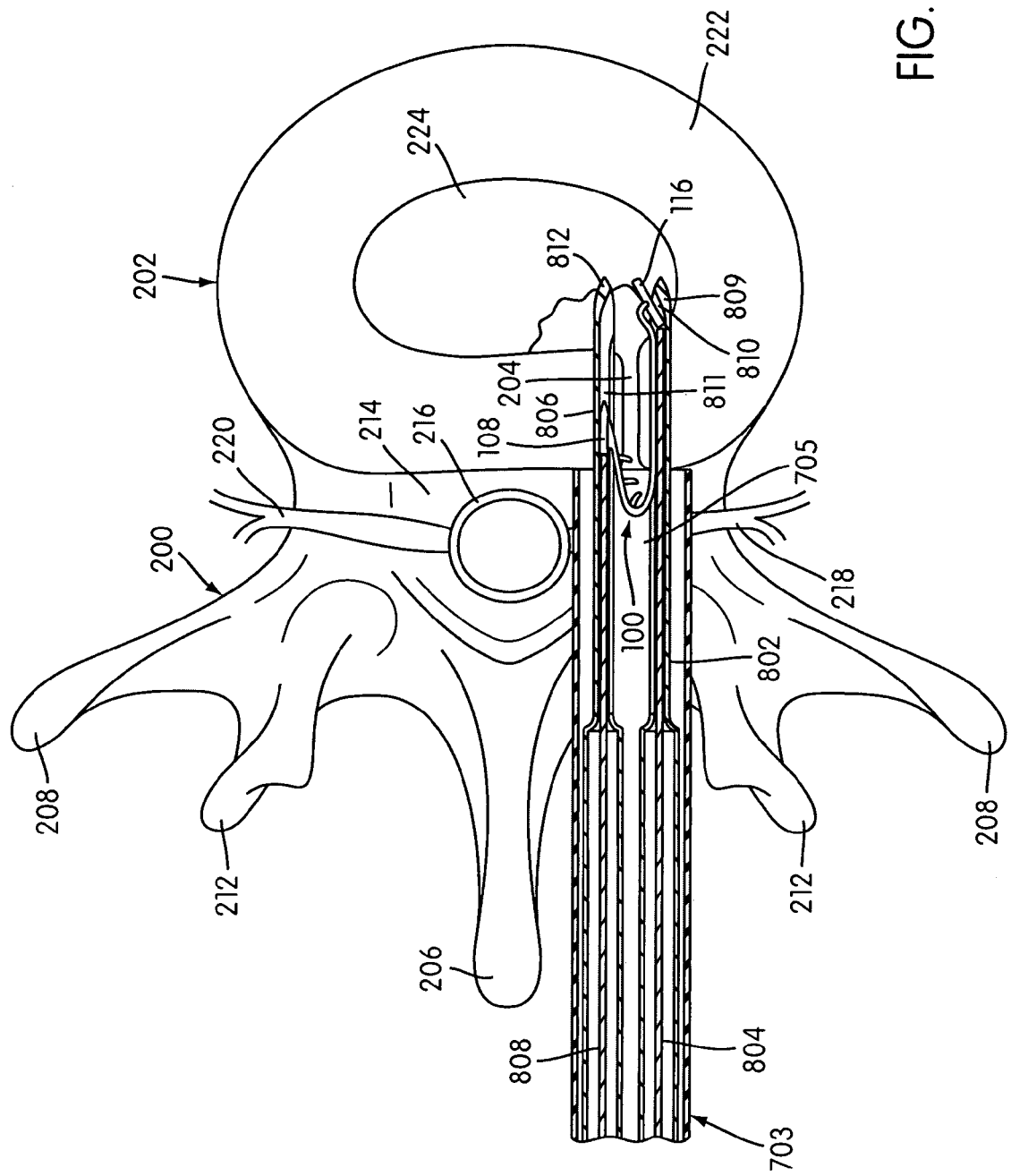
Figure 15:
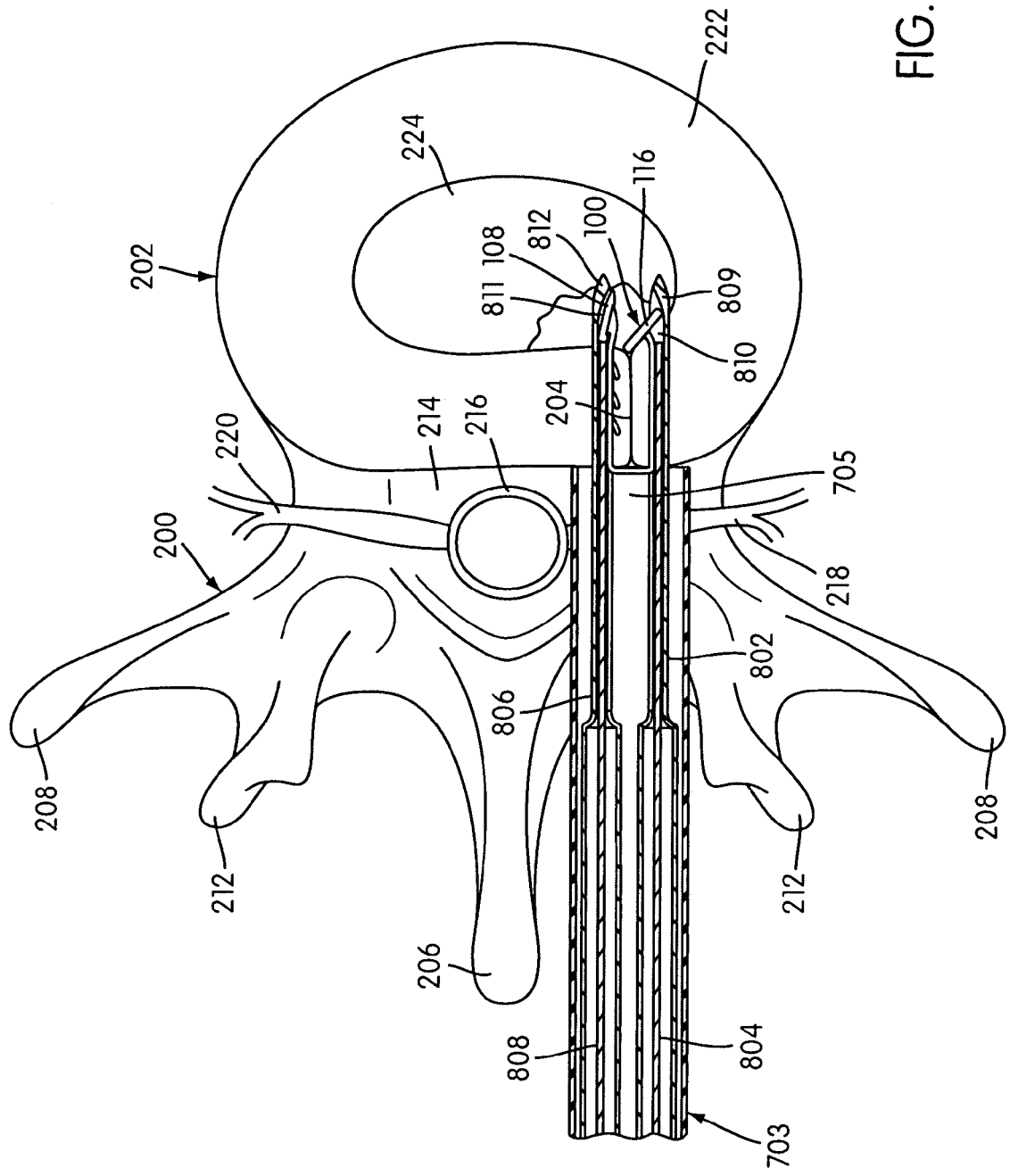

First, as shown in FIG. 14, the movement of the second trigger 706 causes the first push rod 804, which is longer than the second push rod 808, to force the T-portion 104 out of the first penetrating member 802. In some embodiments, this occurs at about the same time that the second push rod 808 establishes initial contact with the barbed portion 102. The arcuate end 809 of the first penetrating member directs the transverse end 116 outward and inward, until it assumes it deployed position generally perpendicular to the T-portion 104, as shown in FIG. 15. Once the transverse end 116 is deployed, the barbed portion 102 is also deployed by the continuing movement of the second follower 916 and the second push rod 808. Once the closure prosthesis 100 reaches the position illustrated in FIG. 15 and has been deployed, penetrating members 802 and 806 are retracted within canula 703 and the entire assembly is preferably withdrawn, as shown in FIG. 16.

The motion of closure prosthesis 100 shown in FIGS. 14 and 15 may have certain advantages. Specifically, because the T-portion 104 is ejected from the first penetrating member 802 and is deployed in the intervertebral disc 202 first, it can act as an anchor on one side of cut or flaw 204 as barbed portion 102 is being implanted. This arrangement also allows T-portion 104 to begin to exert circumferential closing forces on the cut 204 as the barbed portion 102 begins to enter the intervertebral disc 202. Thus, the anchoring of one portion 104 before the other portion 102 may help to create the circumferential forces that cause the cut or flaw 204 to close.

Figure 16:
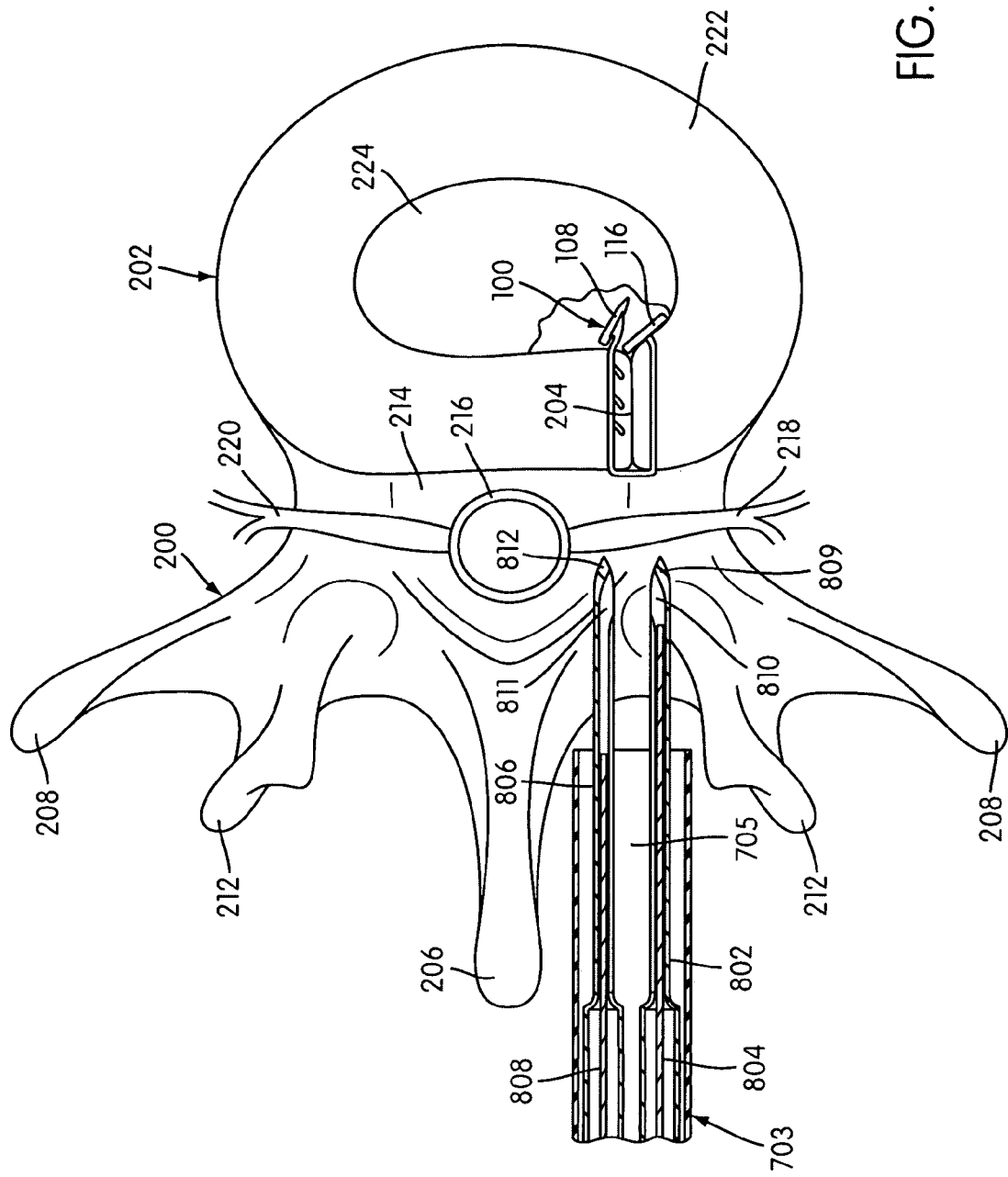

In the final position shown in FIG. 16, closure prosthesis 100 preferably applies a circumferential force proximate cut or flaw 204. In some embodiments, this circumferential force helps to close or secure cut or flaw 204. T-portion 104 is inserted such that transverse end 116 rests in a position generally perpendicular to the remainder of the T-portion 104. The pointed end 108 of the barbed portion 102 can also be inserted to a resting position inside the nucleus purposus 222. However, the position of FIG. 16 is not the only possible operative position for the closure prosthesis 100. For example, the barbed portion 102 need not penetrate all the way through the nucleus purposus 222; instead, any amount of penetration that lodges the barbed portion 102 within the nucleus purposus 222 well enough to close the cut 204 is sufficient.

Additionally, although the cam surfaces 902, 904 and associated structures are adapted in the illustrated embodiment to move the T-portion 104 into the intervertebral disc 202 before the barbed portion 102, this need not always be the case. In other embodiments, if the user found it to be desirable or necessary (for example, to treat a particular type of cut or flaw), cam surfaces 902, 904 and other associated structures could be configured such that the barbed portion 102 is moved into the intervertebral disc 202 first. Moreover, the barbed portion 102 and the T-portion 104 of the closure prosthesis 100 could be advanced into the intervertebral disc 202 at the same time.

FIG. 16 also shows a relative spacing between the barbed portion 102 and the T-portion 104 of the prosthesis 100 that could be adapted to meet particular needs. For example, if a user believed that the nucleus purposus tissue immediately proximate to the cut would not sufficiently anchor the closure prosthesis 100, a wider closure prosthesis 100 could be used, such that its two portions 102, 104 are farther spaced from the cut 204.

Additionally, although a particular application in intervertebral disc repair has been illustrated and described in the foregoing, closure prosthesis 100 and delivery device 700 may be used to close cuts, tears, holes, and incisions in other types of tissue. It is also possible to treat a bulging disc with closure prosthesis 100. In these cases, a protruding bulge or imperfection that has not yet begun to cut or tear can be pressed back towards its original position along the nucleus purposus.

Whatever its ultimate use or features, delivery device 700 is preferably adapted for use in a medical environment. For example, the push rods 804, 808, penetrating members 802, 806, and canula 703 may be detachable from their respective points of connection on the body 702 so as to facilitate autoclaving or other sterilization procedures. Those components may also be interchangeable with rods, penetrating members, and canulas of various sizes, so as to accommodate different surgical and repair situations. Body 702 itself may also be autoclavable or otherwise sterilizable, because the user may grasp it during a repair procedure with a contaminated hand or glove. In some embodiments, delivery device 700 is disposable.

Figure 17:
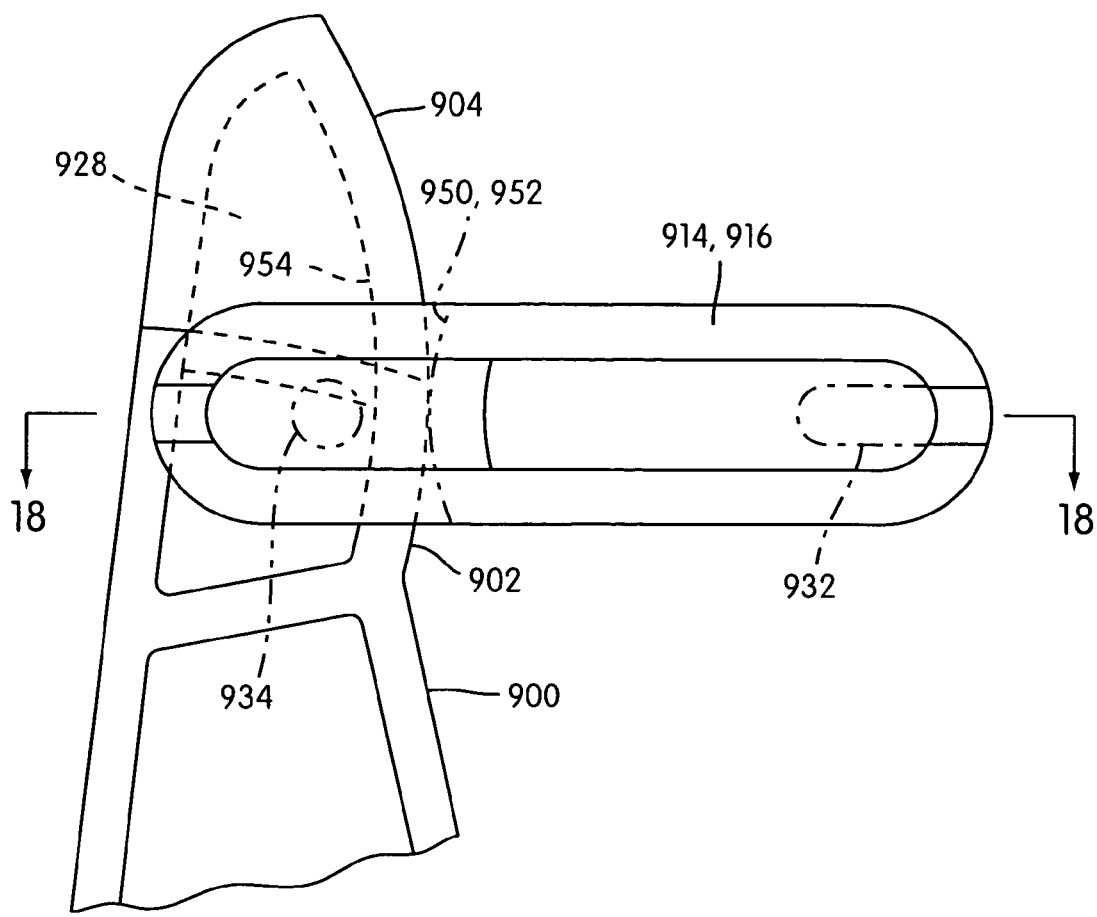
FIG. 17 is a side elevational view of the cams associated with the second trigger mechanism and their associated followers, illustrating the interaction of the cams with the followers.
Figure 18:
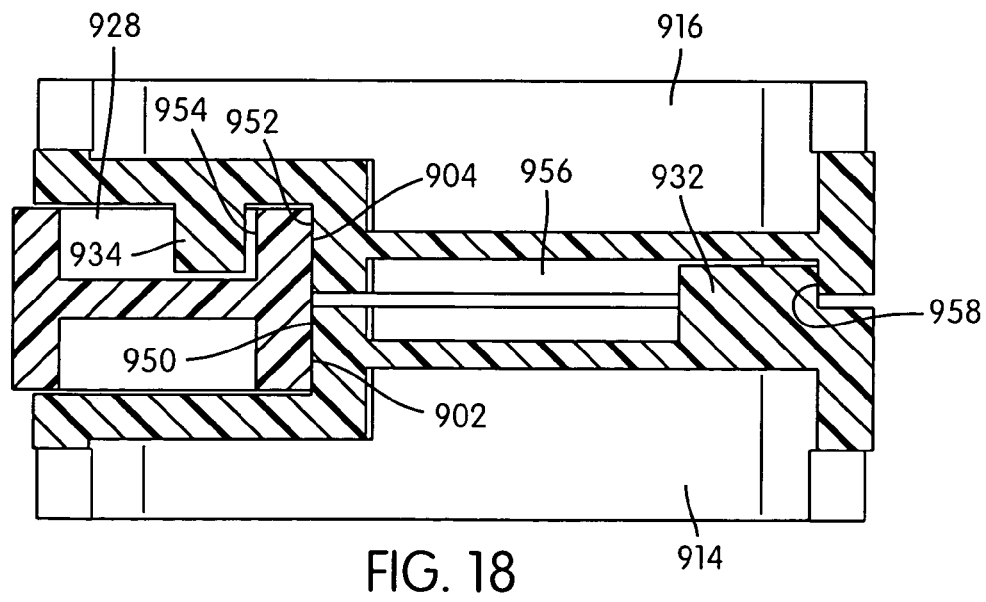
FIG. 18 is a sectional view taken through Line 18-18 of FIG. 17 illustrating a portion of a motion re-setting mechanism in the deployment device.

Some embodiments include provisions for withdrawing or retracting first and second push rods 804 and 808. FIG. 17 is a side elevational view of the upper portion of the coupling member 900 showing the details of one embodiment of a retracting mechanism. FIG. 18 is a sectional view taken through Line 18-18 of FIG. 17. On the side of the upper portion of the coupling member 900 behind second cam surface 904 is a first recessed pocket 928. A pin 934 that is formed integrally with the inside face of the second follower 916 extends into and cooperates with the first recessed pocket 928. The cooperation of the pin 934 with the pocket 928 couples the motion of the coupling member 900 and the motion of the second follower 916.

The motion of first follower 914 and second follower 916 is also preferably associated. Farther forward on the inward face of the second follower 916 is a second recessed pocket 956. A projection 932 on the inward face of first follower 914 is preferably disposed in second recessed pocket 956. As will be appreciated from FIG. 18, the coupling of the first and second followers 914, 916 and the corresponding coupling of the coupling member 900 and the second follower 916 allows relatively free and independent movement of the various components within their normal deployment range of motion. At the same time, the various mechanical associations help to retract first and second push rods 804, 808 when the motion of coupling member 900 is reversed.

Referring to FIGS. 8-11, 17 and 18, when the second trigger 706 is released, the cam spring 910, acting through the coupling member 900, biases second trigger 706 back to its original position, shown in FIG. 8. Simultaneously, as the force of the cam spring 910 acting on the coupling member 900 causes the coupling member 900 to rotate counterclockwise, the rotation of the coupling member 900 moves the first and second cam surfaces 902, 904 rearwardly. When this occurs, an interior bearing surface 954 of the first recessed pocket 928 bears against the pin 934, forcing the second follower 916 to move rearwardly as well. Meanwhile, at the forward end of the second follower 916, an interior bearing surface 958 of the second recessed pocket 956 bears against the projection 932, forcing the first follower 914 to move rearwardly as the second follower 916 moves rearwardly. Additionally, as the second follower 916 travels rearwardly, the ramp shape of its engaging portion 926 lifts the engaging member 920 off of the toothed engaging portion 924 of the first follower 914, thus clearing engaging member 920 from engaging portion 924 of first follower 914, and allowing first follower 914 to move.

As mentioned above, the particular features of the components in deployment device 700 may be selected and adapted to carry out whatever kind of deployment sequence and/or movements are necessary or desired to place the closure prosthesis. In the embodiment described above and illustrated in FIGS. 8-25, cam surfaces are illustrated, the first cam surface 902 is shortened in height, and the first push rod 804 is lengthened in order to produce a deployment movement sequence that deploys the T-portion 104 of the closure first. Other cam profiles and component features may also be chosen.

For example, FIGS. 26-29 are perspective views of the upper terminal portion of a coupling member 900' according to another embodiment. The coupling member 900' carries first and second cam surfaces 902', 904', which cooperate with first and second followers 914', 916' and bear against first and second bearing surfaces 950', 952' on the respective first and second followers 914', 916'. The first and second followers 914', 916' are coupled to first and second push rods 804', 808' which, in this embodiment, have lengths that are substantially identical. The other components of a deployment device that includes the structures shown in FIGS. 26-29 may be assumed to be similar to those shown and described with respect to deployment device 700, although some components may be adapted as necessary to function with coupling member 900'.

In the embodiment of FIGS. 26-29, a differential movement is produced that deploys the T-portion 104 of the closure prosthesis 100 into the tissue first, like in the previous embodiment. However, the differential movement used to deploy the T-portion 104 before the barbed portion 102 is produced by selecting different cam profiles for the first and second cam surfaces 902', 904'. In some embodiments, this cam profile difference can be used in conjunction with first and second push rods 804', 808' that have generally similar lengths.

Figure 26:
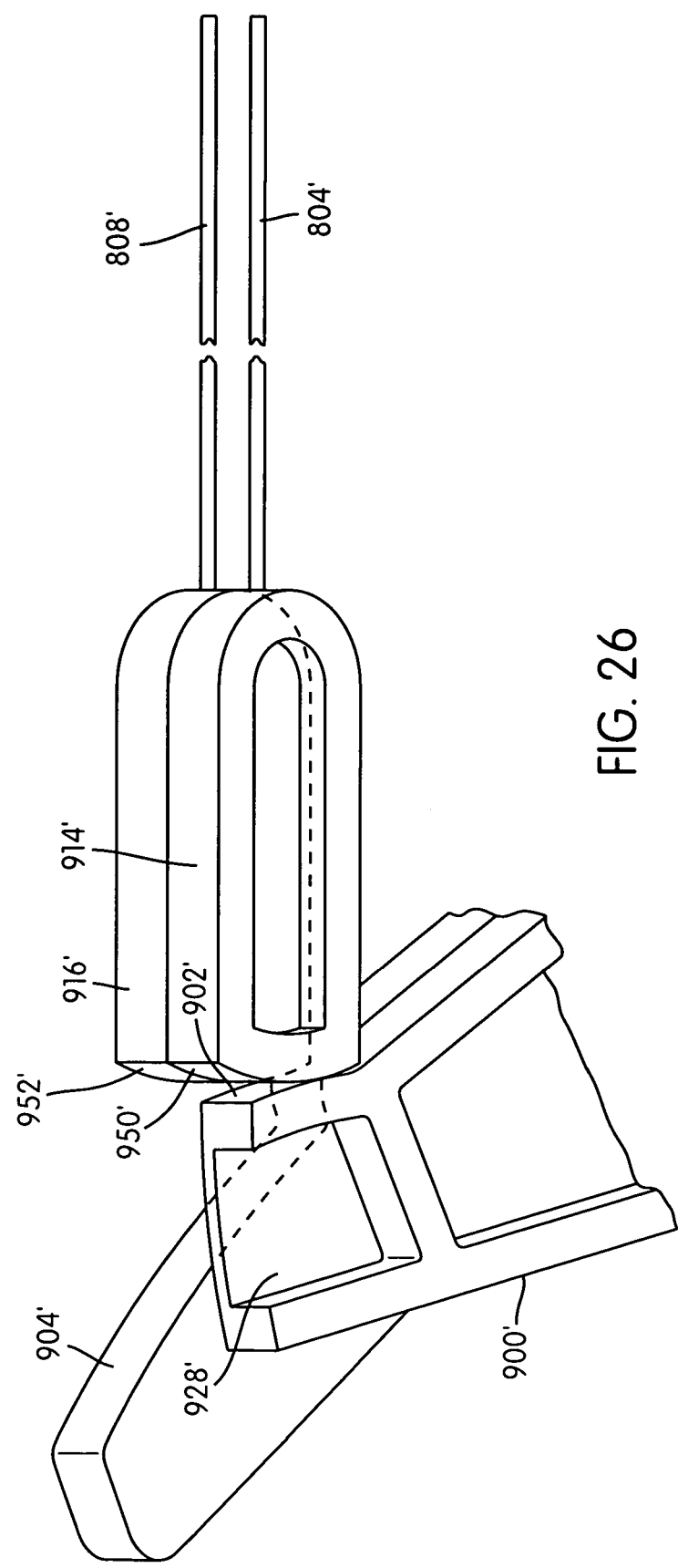
FIGS. 26-29 are perspective views illustrating another embodiment of the cams and followers associated with the second trigger mechanism in isolation, showing the sequence of motion in the cams and followers following actuation of the second trigger mechanism and illustrating schematically the positions of the ends of push rods coupled to the followers.
Figure 27:
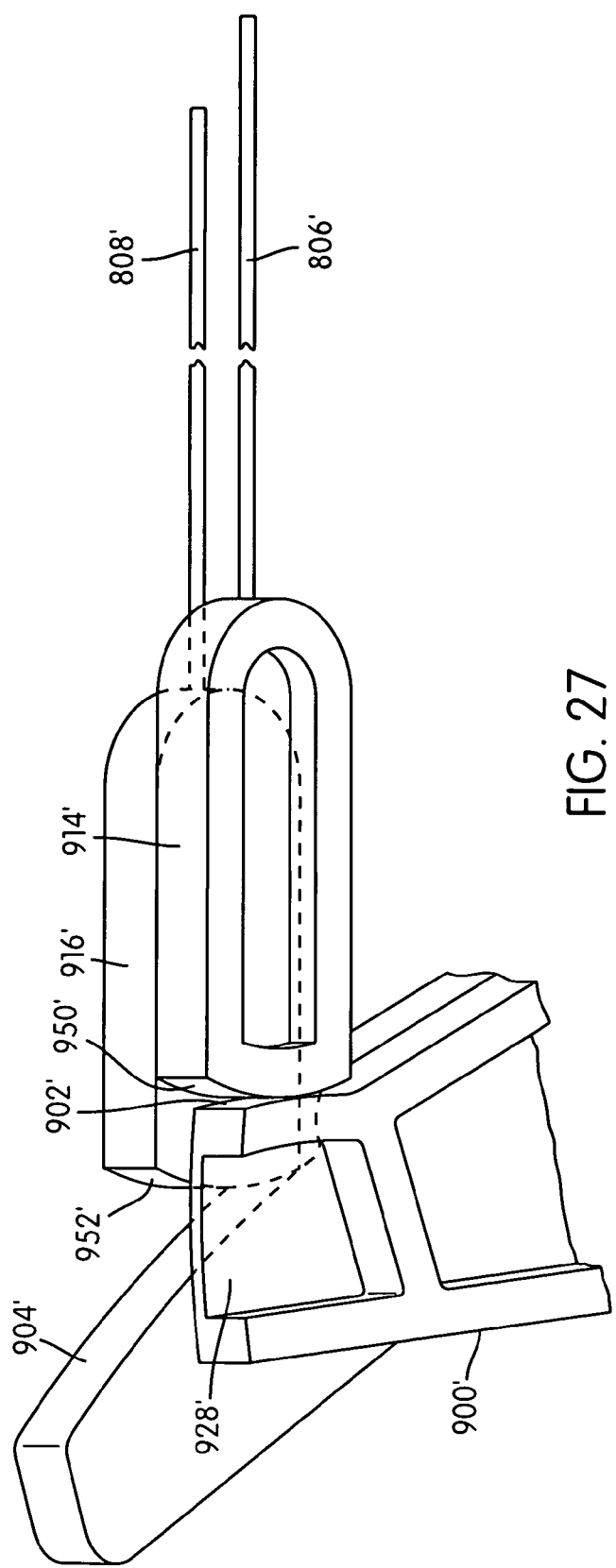
Figure 28:
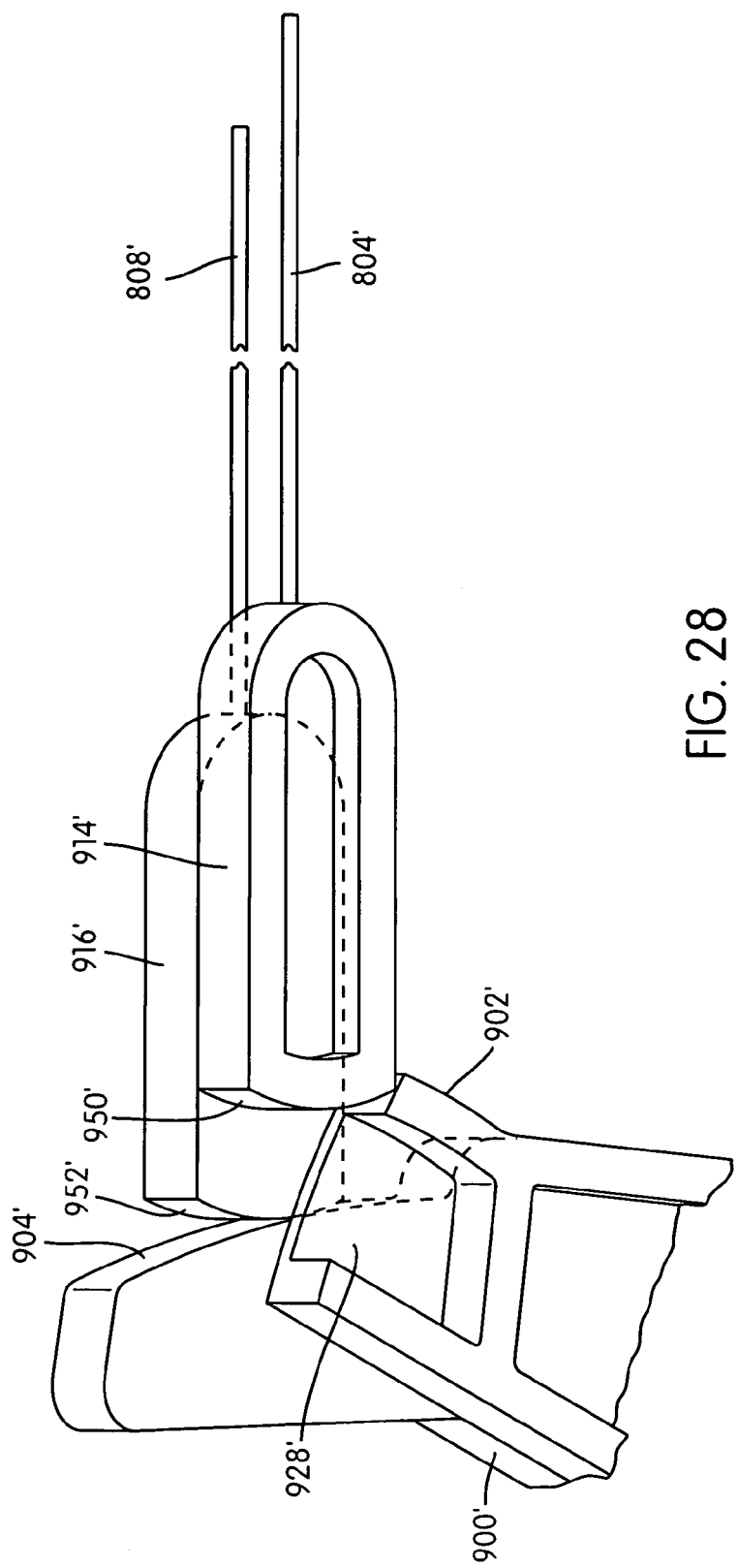
Figure 29:
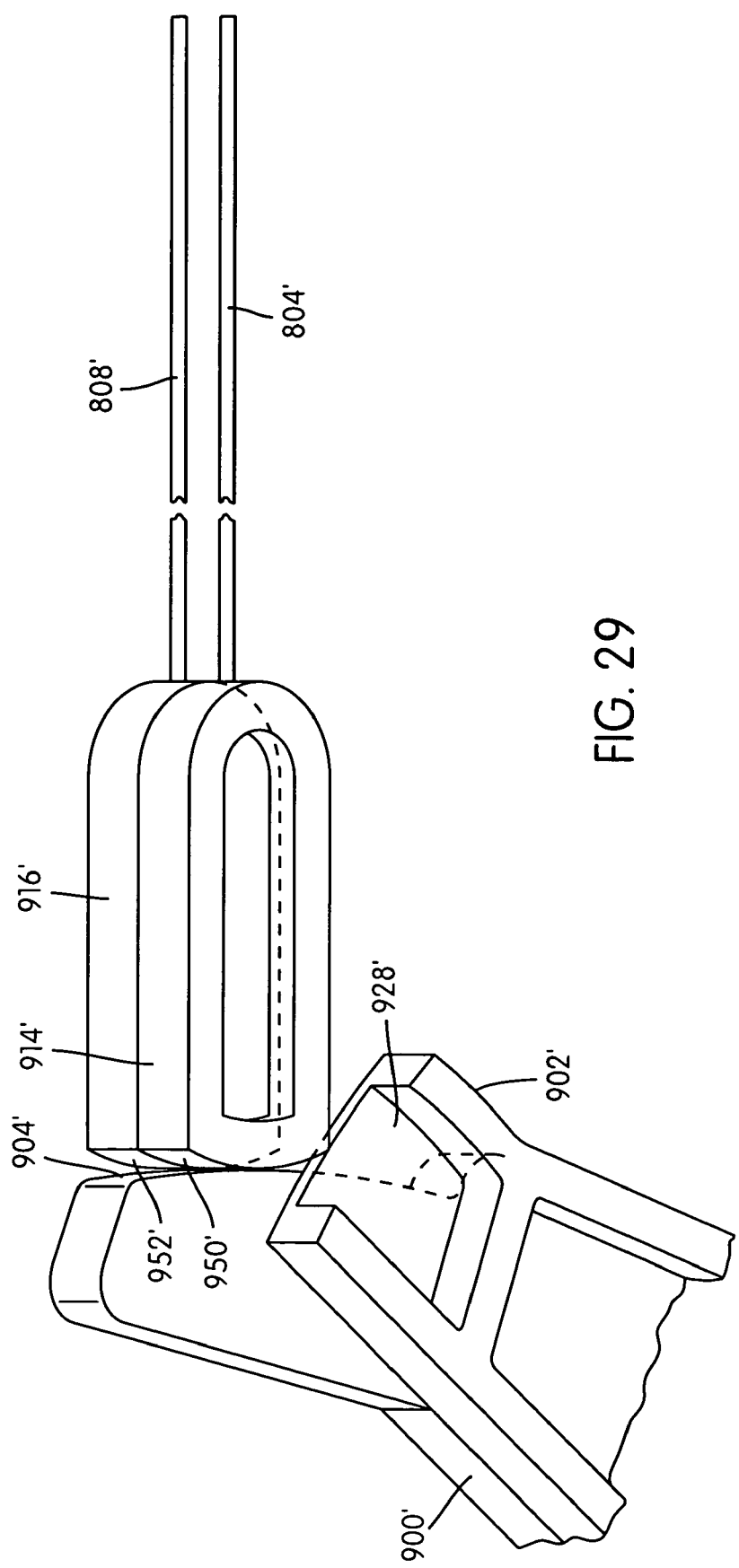

More particularly, as will be appreciated from FIG. 26, the first cam surface 902' is initially positioned in contact with the bearing surface 950' of the first follower 914'. However, the profile of the second cam surface 904' is different and swept back and relatively offset with respect to the first cam surface 902'; thus, the second cam surface 904' does not initially make contact with the bearing surface 952' of the second follower 916'. FIG. 27 shows the initial portion of the movement, during which the first follower 914' advances forward. In the position illustrated in FIG. 27, the second cam surface 904' has just made contact with the bearing surface 952' of the second follower 916'. As shown in FIG. 28, the first cam surface 902' reaches its upper extent and begins to rotate under the first follower 914' when the second follower 916' is in mid-advance. Eventually, the two first and second followers 914', 916' reach the same end position, as shown in FIG. 29.

Although the two embodiments described in detail illustrate the use of similar and dissimilar cam surfaces, it should be appreciated that other linear motion-producing mechanisms may be used within deployment device 700. For example, in alternative embodiments, linkages, gearing, or other linear motion mechanisms could be coupled to the second trigger to produce the desired movements.

Closure prosthesis 100 may be used in a variety of different types of procedures to close a cut, tear, incision, hole, or flaw 204 in an intervertebral disc 202, with or without a deployment device such as deployment device 700. Also, the use of closure prosthesis 100 is not necessarily limited to intervertebal discs. As mentioned above, closure prosthesis 100 can be used to repair tendons, muscles, fascia, bone, cartilage, ligaments or skin in other parts of an organism besides the intervertebal disc region.

More particularly, as was described briefly above, when an intervertebral disc 202 becomes herniated or ruptures because of trauma, the cut, tear, incision, hole, or flaw 204 may have any initial shape, and may also have ragged edges. In order to allow for better closure, and to promote better healing, the operating surgeon or other medical practitioner may make an incision of a particular shape and then use one or more closure prostheses 100 to close the incision.

Figure 30:
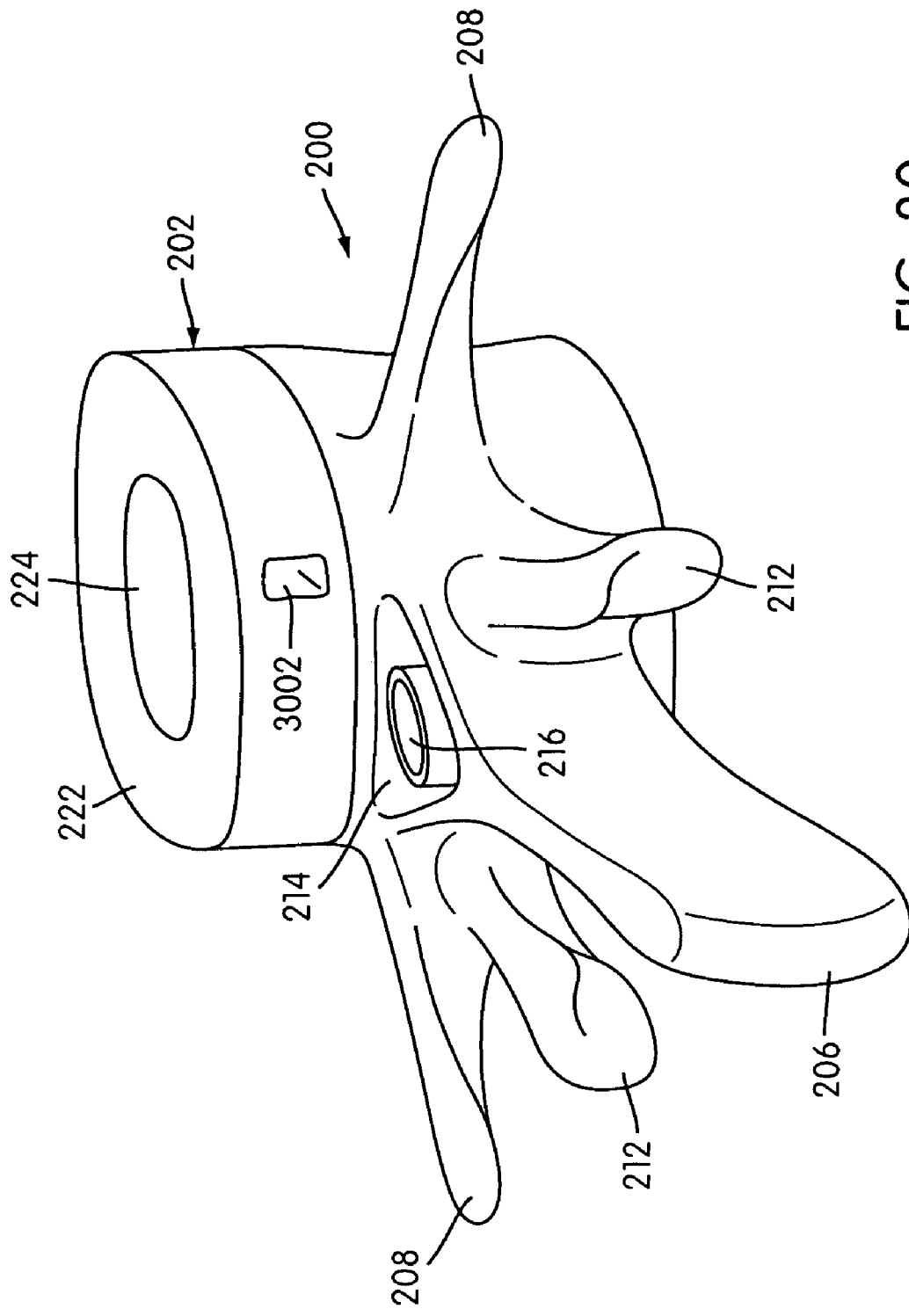
FIG. 30 is a perspective view of a single vertebra and its associated intervertebral disc, illustrating a box-shaped incision in the intervertebral disc.
Figure 31:
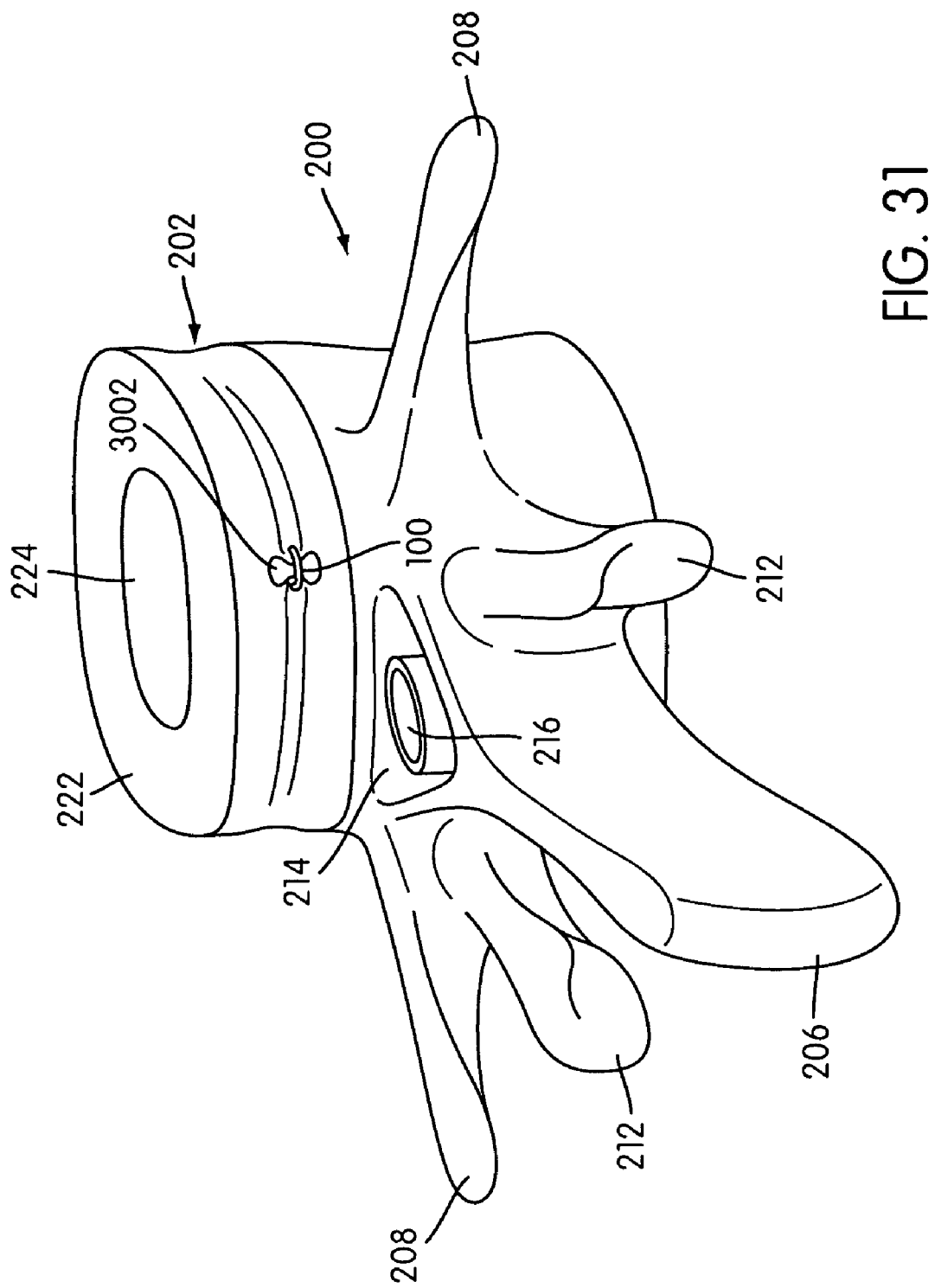
FIG. 31 is a perspective view similar to that of FIG. 30, illustrating a single, horizontally-oriented closure prosthesis closing the incision in the intervertebral disc.

FIG. 30 is a perspective view of a single vertebra 200 and its associated intervertebral disc 202, illustrating a box-shaped incision 3002 in the intervertebral disc 202. The box-shaped incision 204 is formed by cutting a rectangular area out of the nucleus purposus 222. The nucleus purposus 222 is then closed, as shown in FIG. 31, by a first closure prosthesis 100 that spans the box-shaped incision 3002 circumferentially (horizontally in FIG. 31). As shown schematically in FIG. 31, first closure prosthesis can provide a hoop stress to intervertebral disc 202. This hoop stress can also be thought of providing a cinching force about the circumference, either locally or throughout the entire circumference, of intervertebral disc 202. In some cases, this hoop stress helps to axially expand intervertebral disc 202. In other words, the application of circumferential force can help to increase the height (the vertical dimension as shown in FIG. 31) of intervertebral disc 202. In some cases, this axial expansion or increased height is noticeable, and in other cases, this axial expansion or height increase is very slight and difficult to notice. In still other cases, the axial expansion or height increase of intervertebral disc 202 caused by the hoop stress is prevented or restrained by other forces and/or anatomical features that compress the spinal column.

Figure 32:
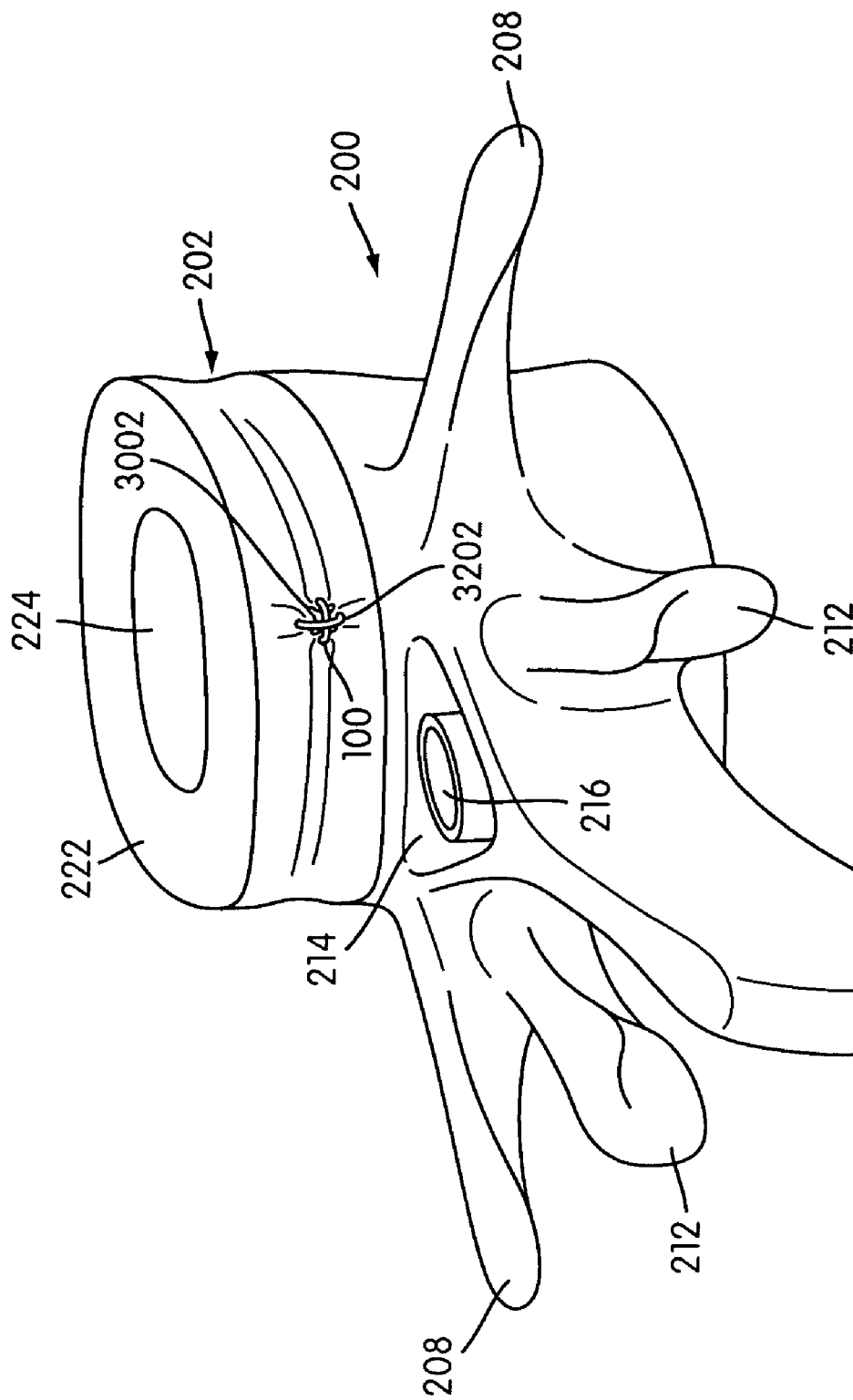
FIG. 32 is a perspective view similar to that of FIG. 30, illustrating a second, vertically-oriented closure prosthesis closing the incision in the intervertebral disc.

In some embodiments, an optional second closure prosthesis 3202 can be used. In some cases, second closure prosthesis 3202 is disposed at an angle different than the position of first closure prosthesis 100. In an exemplary embodiment shown in FIG. 32, second closure prosthesis 3202 is disposed substantially normal to first closure prosthesis 100. In the embodiment shown in FIG. 32, second closure prosthesis 3202 is disposed axially (vertically as shown in FIG. 32) across incision 3002. Before closing the incision 3002, a portion of the volume once occupied by the nucleus purposus 224 in the intervertebral disc 202 may be re-filled with a biocompatible polymer of appropriate mechanical properties so as to improve the elastic response of the intervertebral disc 202. Some examples of suitable biocompatible polymers that can be used to re-fill the volume of the nucleus purposus 224 include: dacron mesh, silicone elastomers, hydrogel, and commercially available nucleus replacements. Other materials can be used as well.

Figure 33:
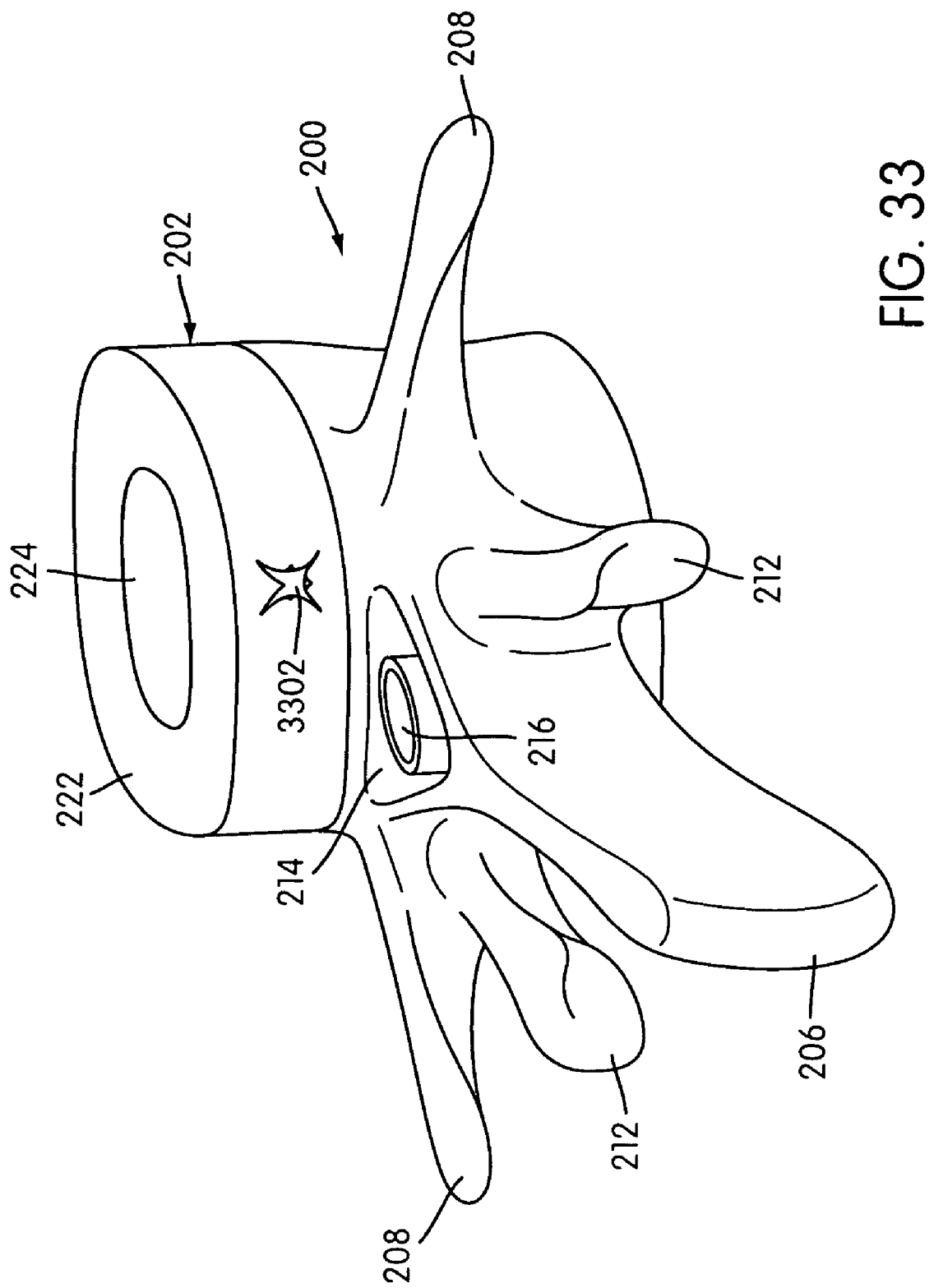
FIG. 33 is a perspective view of a single vertebra and its associated intervertebral disc, illustrating an X-shaped incision in the intervertebral disc.

FIG. 33 is another perspective view of a single vertebra 200 and its associated intervertebral disc 202, illustrating an X-shaped incision 3302 in the intervertebral disc 202. The X-shaped incision 3302 is formed by making two crossed incisions in the nucleus purposus 222. The angular orientation of X-shaped incision 3302 can be varied. A typical X-shaped incision 3302, where the two cuts that form the incision are angled with respect to the circumferential and axial directions, is shown in FIG. 32. In some cases, an X-shaped incision is made where the two cuts are generally aligned with the circumferential and axial directions. In these cases, the X-shaped incision would feature a generally vertical cut and a generally horizontal cut in intervertebral disc 202 as shown in FIG. 32.

Figure 34:
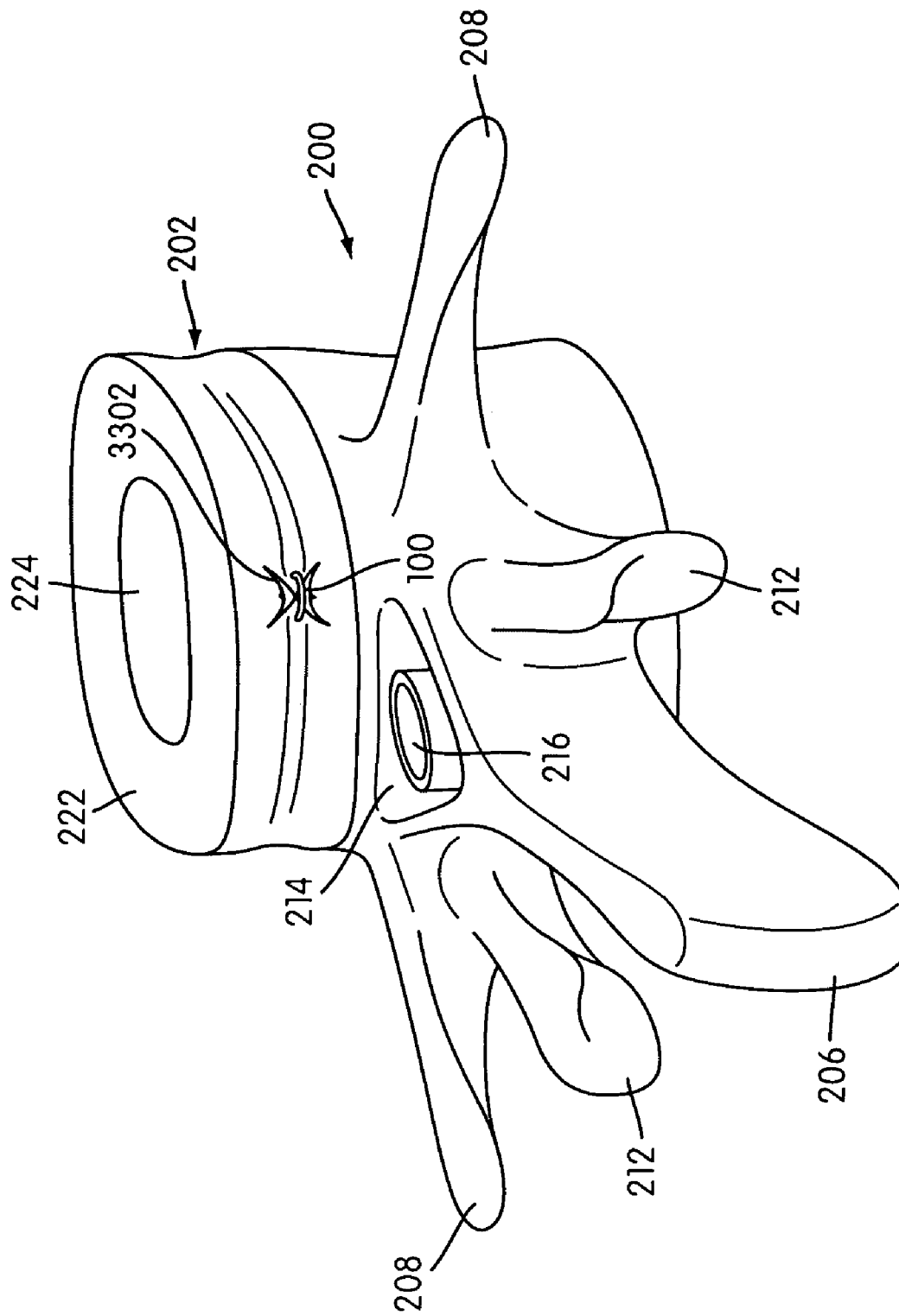
FIG. 34 is a perspective view similar to that of FIG. 33, illustrating a single, horizontally-oriented closure prosthesis closing the incision in the intervertebral disc.

Preferably, X-shaped incision 3302 in nucleus purposus 222 is closed, as shown in FIG. 34, by first closure prosthesis 100 that spans the X-shaped incision 3302 in a first direction. Preferably, first closure prosthesis 100 is disposed in a generally circumferential direction (horizontally in FIG. 34) across X-shaped incision 3302. As shown schematically in FIG. 34, first closure prosthesis 100 can provide a hoop stress to intervertebral disc 202. This hoop stress can also be thought of providing a cinching force about the circumference, either locally or throughout the entire circumference, of intervertebral disc 202. In some cases, this hoop stress helps to axially expand intervertebral disc 202. In other words, the application of circumferential force can help to increase the height (the vertical dimension as shown in FIG. 34) of intervertebral disc 202. In some cases, this axial expansion or increased height is noticeable, and in other cases, this axial expansion or height increase is very slight and difficult to notice. In still other cases, the axial expansion or height increase of intervertebral disc 202 caused by the hoop stress is prevented or restrained by other forces and/or anatomical features that compress the spinal column.

Figure 35:
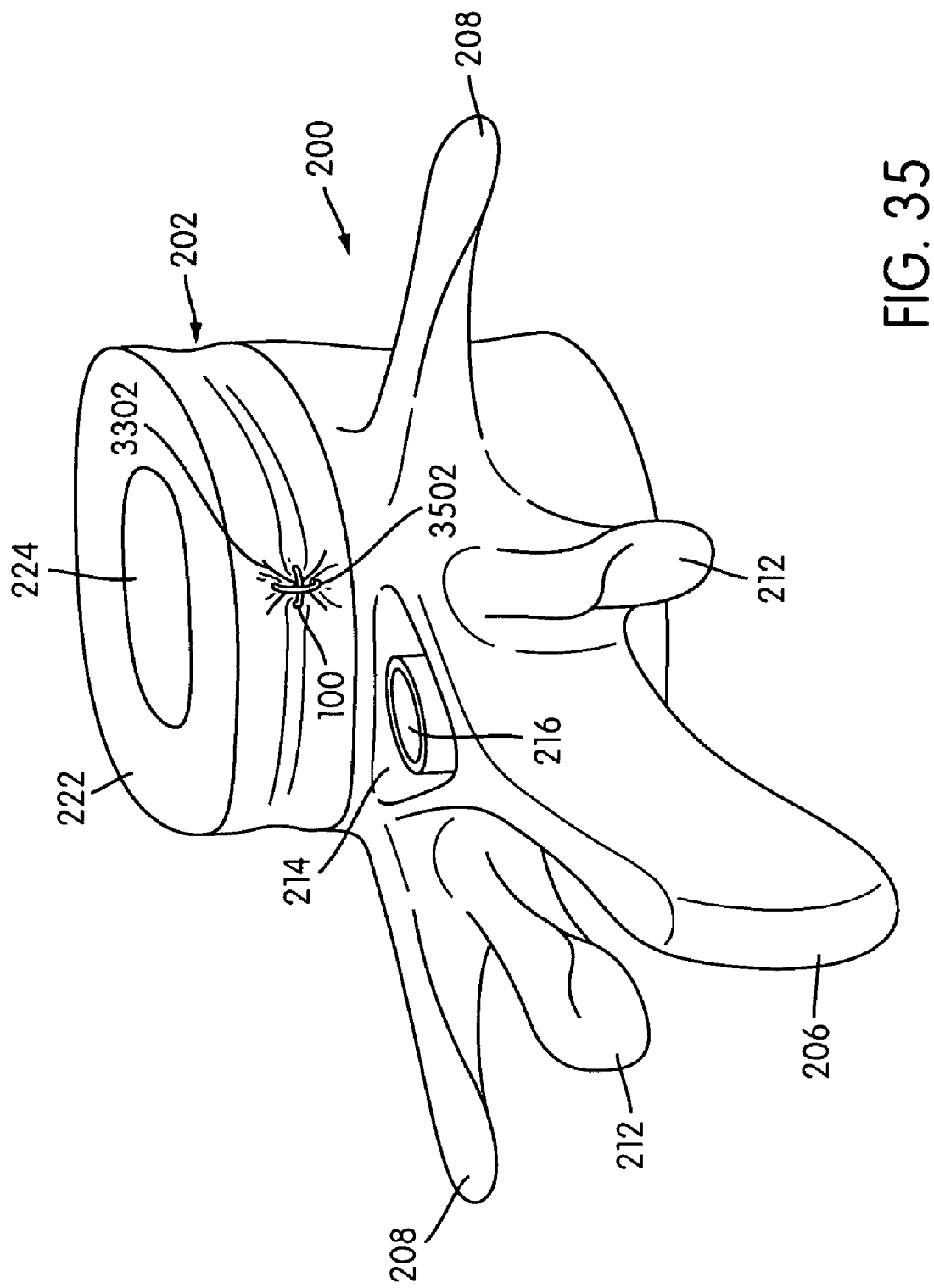
FIG. 35 is a perspective view similar to that of FIG. 33, illustrating a second, vertically-oriented closure prosthesis closing the incision in the intervertebral disc.

In some embodiments, an optional second closure prosthesis 3502 can be used. In some cases, second closure prosthesis 3502 is disposed at an angle different than the position of first closure prosthesis 100. In an exemplary embodiment shown in FIG. 35, second closure prosthesis 3502 is disposed substantially normal to first closure prosthesis 100. In the embodiment shown in FIG. 35, second closure prosthesis 3202 is disposed axially (vertically as shown in FIG. 35) across incision 3302. Before closing the incision 3302, a portion of the volume once occupied by the nucleus purposus 224 in the intervertebral disc 202 may be re-filled with a biocompatible polymer of appropriate mechanical properties so as to improve the elastic response of the intervertebral disc 202.

Figure 36:
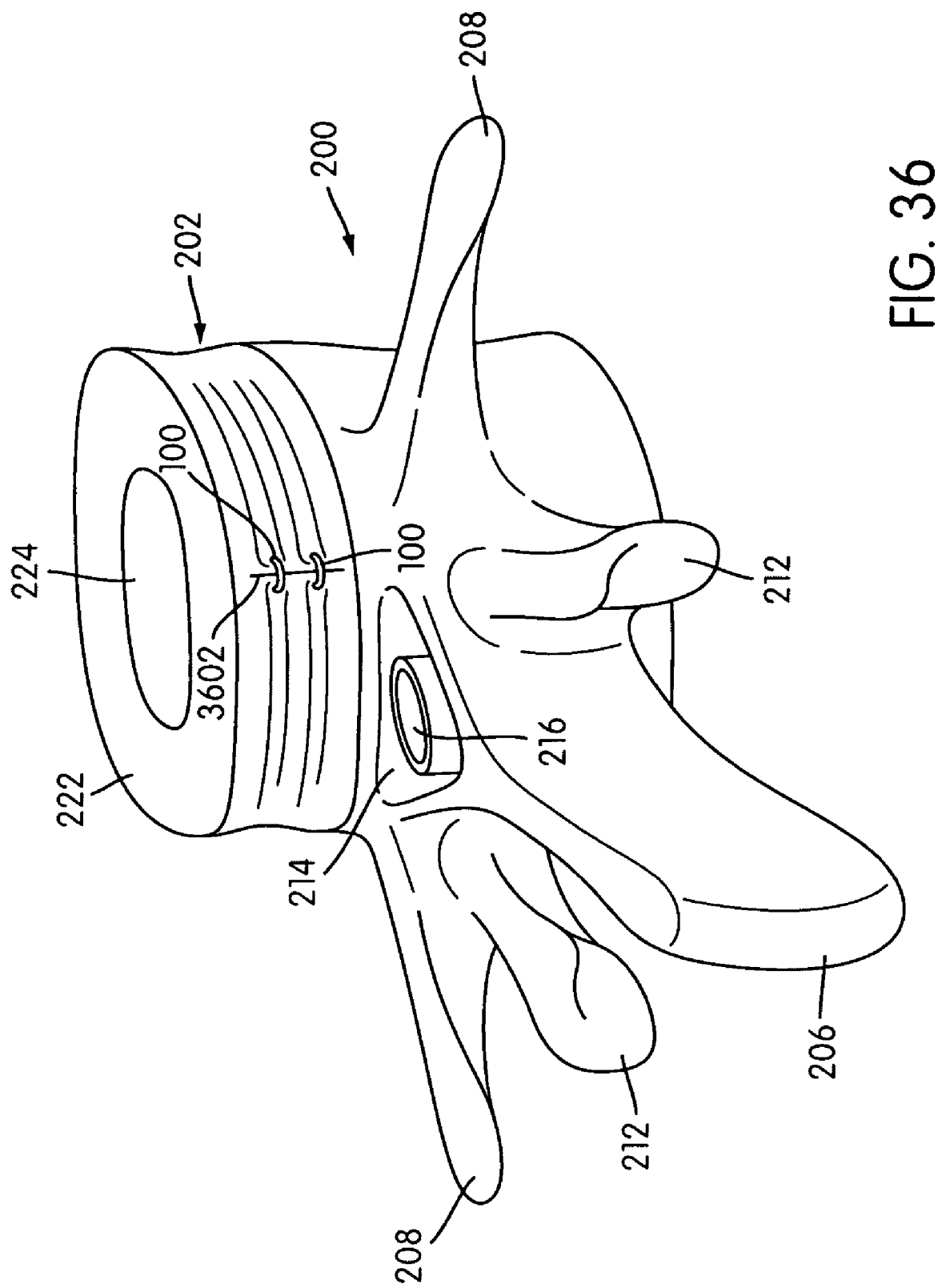
FIG. 36 is a perspective view similar to that of FIG. 30, illustrating two horizontally-oriented closure prostheses closing an incision in an intervertebral disc.

FIG. 36 is another perspective view of a single vertebra 200 and its associated intervertebral disc 202, illustrating a tall vertical incision 3602 in the nucleus purposus 222 that has been closed by two closure prostheses 100 both generally circumferentially disposed (horizontally as shown in FIG. 36) on intervertebral disc 202.

As shown schematically in FIG. 36, first closure prosthesis 100 can provide a hoop stress to intervertebral disc 202. This hoop stress can also be thought of providing a cinching force about the circumference, either locally or throughout the entire circumference, of intervertebral disc 202. In some cases, this hoop stress helps to axially expand intervertebral disc 202. In other words, the application of circumferential force can help to increase the height (the vertical dimension as shown in FIG. 36) of intervertebral disc 202. In some cases, this axial expansion or increased height is noticeable, and in other cases, this axial expansion or height increase is very slight and difficult to notice. In still other cases, the axial expansion or height increase of intervertebral disc 202 caused by the hoop stress is prevented or restrained by other forces and/or anatomical features that compress the spinal column.

As shown in FIG. 36, depending on the nature of the incision, it may not be necessary to provide a closure prosthesis with a different angular orientation. Although FIG. 36 shows a generally axial orientation (vertical in FIG. 36) of incision 3602, it is also possible that incision 3602 be angled with respect to the particular incision 3602 shown in FIG. 36. In other embodiments, it is possible to provide more than two closure prosthesis in similar or different angular orientations with respect to an incision.

Although surgical and prosthesis deployment methods may vary with the patient's particular diagnosis or injury, as well as at the discretion of the operating surgeon, placing a horizontal closure prosthesis 100 first may help to provide the circumferential stress to close the intervertebral disc 202, and may also help to increase the axial height of the intervertebral disc 202. Additionally, although two closure prostheses 100 have been used to close some of the incisions shown in the previous figures, any number of closure prostheses 100 may be used, and the closure prostheses 100 that are used may be of any size.

Figure 37:
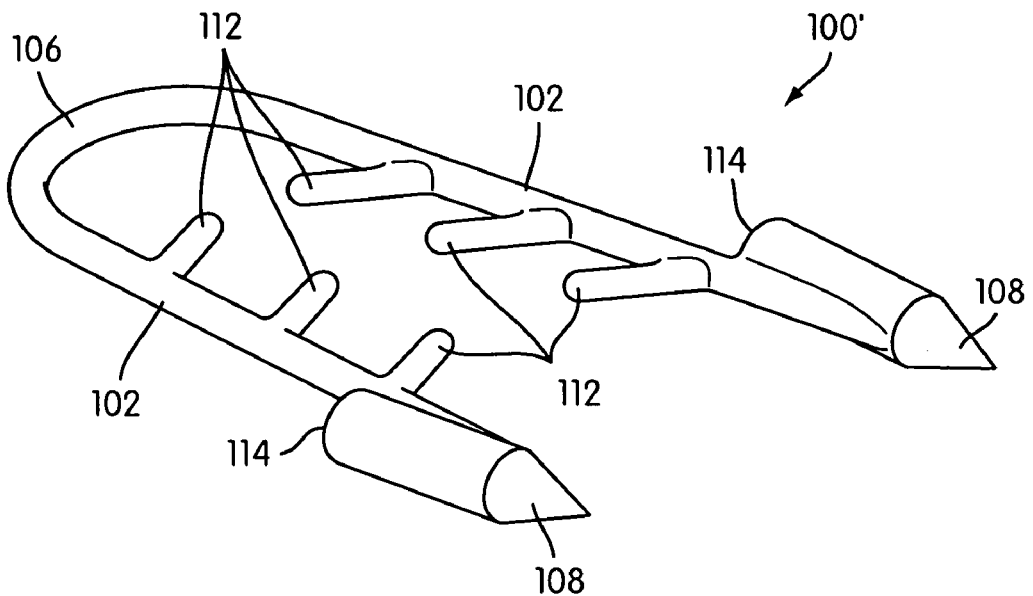
FIG. 37 is a perspective view of an embodiment of a closure prosthesis with two barbed ends.

As was noted above, the closure prosthesis 100 may also be varied in a number of ways for different applications. For example, FIG. 37 illustrates an embodiment of a closure prosthesis 100' that has two barbed portions 102 and no T-portion 104. The structure of closure prosthesis 100' is otherwise generally similar to that of closure prosthesis 100.

Figure 38:
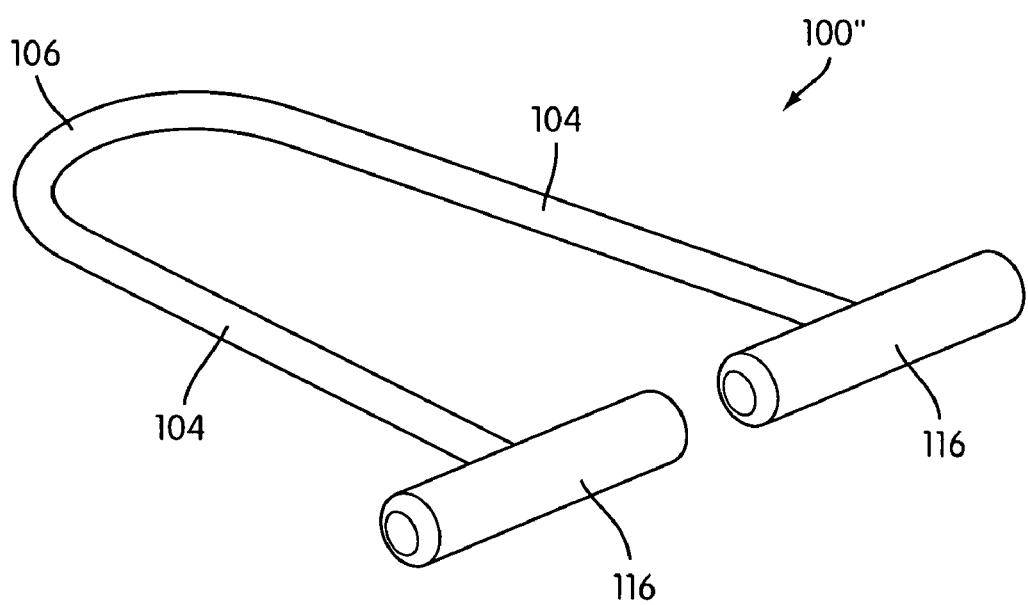
FIG. 38 is a perspective view of an embodiment of a closure prosthesis with two transverse ends.

FIG. 38 illustrates an embodiment of a closure prosthesis 100" that has two T-portions 104 and no barbed portion 102. The structure of closure prosthesis 100" is otherwise generally similar to that of closure prosthesis 100.

While various embodiments of the invention have been described, the description is intended to be exemplary, rather than limiting and it will be apparent to those of ordinary skill in the art that many more embodiments and implementations are possible that are within the scope of the invention. Accordingly, the invention is not to be restricted except in light of the attached claims and their equivalents. Also, various modifications and changes may be made within the scope of the attached claims.

What is claimed is:

1. A method for repairing an imperfection on a disc associated with a spinal column comprising the steps of:
    puncturing a first portion of the disc on a first side of the imperfection with a first penetrating member, wherein the first penetrating member carries a substantial portion of a first end of a prosthesis within a channel formed in the first penetrating member;
    inserting the first end portion of the prosthesis into the first portion of the disc by moving a trigger a first distance to eject the first end portion of the prosthesis from the first channel;
    the prosthesis having a central portion connected to the first end portion and a second end portion connected to the central portion; the first end portion having a first anchoring device, and the second end portion having a second anchoring device;
    puncturing a second portion of the disc that is circumferentially spaced from the first portion of the disc on a second side of the imperfection with a second penetrating member, wherein the second penetrating member carries a substantial portion of the second end portion within a second channel formed in the second penetrating member;
    inserting the second end portion of the prosthesis into the second portion of the disc by moving the trigger a second distance to eject the second end portion of the prosthesis from the second channel, wherein the first end portion of the prosthesis remains substantially stationary while the second end portion is being ejected;
    spanning the imperfection with the central portion of the prosthesis; and
    wherein the second end portion of the prosthesis is further inserted into the disc thereby drawing the first side of the imperfection closer to the second side of the imperfection.

2. The method according to claim 1, wherein continued motion of the trigger substantially closes the imperfection.

3. The method according to claim 1, wherein the first end portion includes at least one projection extending away from the first end portion.

4. The method according to claim 1, wherein the imperfection is a bulge on the disc.

5. The method according to claim 1, wherein the prosthesis in an installed position provides a circumferential force on the disc.

6. The method according to claim 1, wherein the prosthesis provides a hoop stress on the disc.

7. The method according to claim 1, wherein the prosthesis helps to maintain an axial height of the disc.

8. The method according to claim 1, wherein the prosthesis helps to increase an axial height of the disc.

9. A method for repairing an imperfection on a disc associated with a spinal column comprising the steps of:
- initially inserting a prosthesis into the disc by moving a first trigger a first distance to insert a first penetrating member into a first portion of the disc, wherein the first penetrating member includes a hollow interior portion, and wherein a first end portion of the prosthesis is carried within the hollow interior portion;
- inserting the first end portion of the prosthesis into the first portion of the disc by moving a second trigger a first distance to eject the first portion of the disc from the first penetrating member;
- the prosthesis having a central portion connected to the first end portion and also connected to a second end portion, wherein the second end portion is carried within a hollow interior portion of a second penetrating member;
- inserting the second end portion of the prosthesis into a second portion of the disc by continuing to move the second trigger a second distance to eject the second end portion of the prosthesis from the second penetrating member;
- wherein the motion of the first end portion of the prosthesis is independent from the motion of the second end portion of the prosthesis; and
- wherein the second end portion of the prosthesis is further inserted into the disc thereby drawing the first side of the imperfection closer to the second side of the imperfection.

10. The method according to claim 9, wherein the step of inserting the first end portion of the prosthesis includes the step of deploying the first end portion from a first penetrating member.

11. The method according to claim 10, wherein the movement of the first trigger the first distance moves a first push rod, which in turn, moves the first end portion away from the first penetrating member.

12. The method according to claim 9, wherein the step of inserting the second end portion of the prosthesis includes the step of deploying the second end portion from a second penetrating member.

13. The method according to claim 12, wherein the movement of the second trigger the second distance moves a second push rod, which in turn, moves the second end portion away from the second penetrating member.

14. The method according to claim 9, wherein the first end portion is associated with a first penetrating member connected to a deployment device and wherein the second end portion is associated with a second penetrating member connected to the deployment device;
- and wherein the first trigger and the second trigger are both connected to the deployment device;
- wherein both the first end portion and the second end portion can be deployed with a single hand moving the second trigger of the deployment device.

15. A method for repairing an imperfection on a disc associated with a spinal column using a single hand comprising the steps of:
- placing a cannula proximate to the imperfection;
- delivering, through the cannula, a first penetrating member and a second penetrating member;
- the first penetrating member and the second penetrating member both being associated with a deployment device, the deployment device including a trigger;
- the first penetrating member retaining a first end portion of a prosthesis within a first channel formed in the first penetrating member and the second penetrating member retaining a second end portion of the prosthesis within a second channel formed in the second penetrating member;
- deploying the first end portion of the prosthesis by moving the trigger a first distance, wherein the second end portion remains within the second channel while the first end portion is being deployed; and
- deploying the second end portion of the prosthesis by continuing to move the trigger a second distance, wherein the first end portion remains substantially stationary within the disc while the second end portion is being deployed.

16. The method according to claim 15, wherein the first end portion of the prosthesis is disposed within the first penetrating member.

17. The method according to claim 16, wherein movement of the trigger the first distance moves a first push rod, disposed within the first penetrating member, which in turn, moves the first end portion away from the first penetrating member.

18. The method according to claim 15, wherein the first end portion of the prosthesis is initially disposed within the first penetrating member.

19. The method according to claim 17, wherein movement of the trigger the second distance moves a second push rod disposed within the second penetrating member, which in turn, moves the second end portion away from the second penetrating member.

* * * * *